United States Patent
Jung et al.

(10) Patent No.: US 10,550,011 B2
(45) Date of Patent: Feb. 4, 2020

(54) STERILIZATION MODULE, WATER PURIFICATION DEVICE, AND SYSTEM COMPRISING WATER PURIFICATION DEVICE

(71) Applicant: SEOUL VIOSYS CO., LTD., Ansan-si (KR)

(72) Inventors: Woong Ki Jung, Ansan-si (KR); Sang Hyun Chang, Ansan-si (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 0 days.

(21) Appl. No.: 15/936,274

(22) Filed: Mar. 26, 2018

(65) Prior Publication Data
US 2018/0215634 A1   Aug. 2, 2018

Related U.S. Application Data

(63) Continuation of application No. PCT/KR2016/008610, filed on Aug. 4, 2016.

(30) Foreign Application Priority Data

Sep. 25, 2015 (KR) .................. 10-2015-0136763
Nov. 2, 2015 (KR) .................. 10-2015-0153423
Apr. 11, 2016 (KR) .................. 10-2016-0044348

(51) Int. Cl.
*C02F 1/32* (2006.01)
*A61L 2/10* (2006.01)
*A61L 2/26* (2006.01)

(52) U.S. Cl.
CPC ............... *C02F 1/325* (2013.01); *A61L 2/10* (2013.01); *A61L 2/26* (2013.01); *A61L 2202/11* (2013.01);
(Continued)

(58) Field of Classification Search
CPC .......... A61L 2202/11; A61L 2/10; A61L 2/26; C02F 1/32; C02F 1/325; C02F 2201/3221; C02F 2201/3228
See application file for complete search history.

(56) References Cited

U.S. PATENT DOCUMENTS

| | | | |
|---|---|---|---|
| 5,030,125 A * | 7/1991 | Toma .................. | H01R 33/975 313/51 |
| 6,403,030 B1 * | 6/2002 | Horton, III .............. | A61L 2/10 210/748.11 |

(Continued)

FOREIGN PATENT DOCUMENTS

| | | |
|---|---|---|
| DE | 202012101818 U1 | 6/2012 |
| KR | 20-0417938 Y1 | 6/2006 |

(Continued)

OTHER PUBLICATIONS

International Search Report in PCT/KR2016/008610, dated Nov. 1, 2016.

(Continued)

*Primary Examiner* — Wyatt A Stoffa
(74) *Attorney, Agent, or Firm* — Perkins Coie LLP

(57) ABSTRACT

In one aspect, a sterilization apparatus is provided to include a flow channel body comprising an inflow unit configured to provide an inflow channel through which water flows in one direction, a discharge unit configured to provide a discharge channel through which water is discharged, and a bypass channel unit configured to provide a bypass channel through which water bypasses in a different direction from the direction of the water flowing in the inflow unit; a mounting unit formed on the flow channel body and configured to provide an installation space connected to the bypass channel, a UV light emitting unit disposed in the installation space and configured to emit UV light towards the bypass (Continued)

channel; and a holder coupled to the mounting unit and securing the UV light emitting unit inside the mounting unit.

16 Claims, 20 Drawing Sheets

(52) U.S. Cl.
CPC ............... *C02F 2201/3221* (2013.01); *C02F 2201/3227* (2013.01); *C02F 2201/3228* (2013.01); *C02F 2303/04* (2013.01)

(56) References Cited

U.S. PATENT DOCUMENTS

| | | | | |
|---|---|---|---|---|
| 6,500,346 | B1* | 12/2002 | Taghipour | A61L 2/08 |
| | | | | 210/198.1 |
| 7,045,102 | B2* | 5/2006 | Fraser | A61L 2/10 |
| | | | | 210/748.1 |
| 9,592,374 | B2* | 3/2017 | Muse | A61M 39/16 |
| 2003/0010927 | A1* | 1/2003 | Wedekamp | A61L 2/10 |
| | | | | 250/436 |
| 2003/0071225 | A1* | 4/2003 | Boehme | C02F 1/325 |
| | | | | 250/432 R |
| 2005/0069463 | A1* | 3/2005 | Kurtz | A61L 9/20 |
| | | | | 422/121 |
| 2010/0209294 | A1* | 8/2010 | Owen | A61L 9/205 |
| | | | | 422/24 |
| 2010/0237254 | A1* | 9/2010 | Mason | A61L 2/10 |
| | | | | 250/435 |
| 2010/0264329 | A1* | 10/2010 | Vardiel | C02F 1/325 |
| | | | | 250/436 |
| 2013/0234037 | A1* | 9/2013 | Moglan | A61L 2/10 |
| | | | | 250/432 R |
| 2014/0158905 | A1* | 6/2014 | Hoang | C02F 1/325 |
| | | | | 250/435 |
| 2015/0129776 | A1* | 5/2015 | Boodaghians | C02F 1/325 |
| | | | | 250/432 R |
| 2015/0314024 | A1* | 11/2015 | Khan | C02F 1/325 |
| | | | | 250/435 |
| 2016/0052801 | A1* | 2/2016 | Kruger | C02F 1/325 |
| | | | | 250/494.1 |
| 2017/0022073 | A1* | 1/2017 | Penhale | A61L 2/08 |

FOREIGN PATENT DOCUMENTS

| | | |
|---|---|---|
| KR | 10-1072592 B1 | 10/2011 |
| KR | 10-2012-0012710 A | 2/2012 |
| WO | 2014115146 A1 | 7/2014 |

OTHER PUBLICATIONS

Supplementary Partial European Search Report from corresponding European Application No. 16848793 dated Aug. 1, 2019 (7 pages).

* cited by examiner

STERILIZATION MODULE, WATER PURIFICATION DEVICE, AND SYSTEM COMPRISING WATER PURIFICATION DEVICE

CROSS-REFERENCE TO RELATED APPLICATION(S)

This patent document is a continuation of International Patent Application No. PCT/KR2016/008610, filed Aug. 4, 2016, entitled "STERILIZATION MODULE, WATER PURIFICATION DEVICE, AND SYSTEM COMPRISING WATER PURIFICATION DEVICE," which claims priority to and benefit of Korean Patent Application No. 10-2015-0136763, filed Sep. 25, 2015, Korean Patent Application No. 10-2015-0153423, filed Nov. 2, 2015, and Korean Patent Application No. 10-2016-0044348, filed Apr. 11, 2016.

TECHNICAL FIELD

Embodiments of the disclosed technology relate to a sterilization module, a water purifier, and a system including the water purifier.

BACKGROUND

UV light has different properties depending upon UV wavelength and is applied to a sterilizing device based on the properties thereof depending on UV wavelength. A mercury (Hg) lamp is generally used for a sterilizing device using UV light. Sterilization is performed using ozone ($O_3$) generated by wavelengths emitted from the mercury lamp. However, since the mercury (Hg) lamp contains mercury, there can be a problem of environmental contamination with increasing use time of the mercury lamp.

Recently, a sterilizing device using various UV light has been developed and provided. In addition, such a sterilizing device has been applied to a variety of sterilizing objects. Such a sterilizing device is embedded in an apparatus, such as a refrigerator, a washing machine, a humidifier, or a water purifier.

SUMMARY

Embodiments of the disclosed technology provide a sterilization module capable of purifying water, a water purifier, and a system including the water purifier.

Embodiments of the disclosed technology provide a sterilization module allowing easy replacement of malfunctioning components, a water purifier, and a system including the water purifier.

In accordance with one embodiment of the disclosed technology, a sterilization module includes: a flow channel body having a flow channel through which water flows; a UV light emitting unit emitting UV light towards the flow channel; a mounting unit receiving the UV light emitting unit and formed on the flow channel body to connect an installation space to the flow channel, the UV light emitting unit being disposed in the installation space; and a holder coupled to the mounting unit and securing the UV light emitting unit inside the mounting unit.

The flow channel body may include: an inflow unit defining an inflow channel through which water flows in one direction; and a discharge unit connected to the inflow channel and defining a discharge channel extending from the inflow channel in another direction to form the flow channel together with the inflow channel.

The inflow unit and the discharge unit may be connected to each other in an "L" shape.

A joint between the inflow unit and the discharge unit may be formed with a penetrating portion, and the mounting unit may be formed at the joint between the inflow unit and the discharge unit to protrude outward from the flow channel body such that the installation space communicates with the penetrating portion.

The UV light emitting unit may include a substrate mounted on the mounting unit and a UV light emitting device mounted on the substrate and emitting UV light towards the flow channel in the installation space.

The UV light emitting device may be disposed on an imaginary bisector bisecting an internal angle defined between the inflow channel and the discharge channel to emit UV light towards the inflow channel and the discharge channel, and the inflow unit may be connected to the discharge unit such that the inflow channel and the discharge channel are exposed to UV light in a UV light radiation angle range of the UV light emitting device.

The sterilization module may further include a protective cover provided to the mounting unit to shield a space between the flow channel and the UV light emitting device and formed of a UV light transmissive material.

The protective cover may include at least one of quartz, a poly(methyl methacrylate) resin, and a fluorine-based polymer resin having high UV light transmittance.

The sterilization module may further include a spacer disposed between the substrate and the protective cover to form a space between the UV light emitting device and the protective cover.

An inner protrusion may be formed between the flow channel body and the mounting unit to protrude into the mounting unit, and a sealing member may be disposed between the inner protrusion and the protective cover to seal a gap between the protective cover and the flow channel body.

The holder may be coupled to an inner peripheral surface of the mounting unit and compress the substrate towards the inner protrusion to secure the UV light emitting unit inside the mounting unit.

The sterilization module may further include a cable connected to the substrate to connect the substrate to a power supply, wherein the holder is formed with a cable hole through which the cable passes towards the substrate.

The UV light emitting device may emit UV light having a peak wavelength in the range of 200 nm to 280 nm.

The sterilization module may further include a reflector reflecting UV light emitted from the UV light emitting unit towards the flow channel.

The reflector may be realized by aluminum or stainless steel on an inner peripheral surface of the flow channel body defining the flow channel therein.

In accordance with another embodiment of the disclosed technology, a water purifier includes: a water reservoir storing purified water; a water pipe connected to the water reservoir; a water-intake cork opened or closed to allow selective discharge of water supplied through the water pipe; and the sterilization module disposed between the water pipe and the water-intake cork and sterilizing water flowing towards the water-intake cork through the water pipe.

The water purifier may further include: a detection unit detecting whether the water-intake cork is open or closed; and a controller controlling operation of the sterilization module depending upon a detection result of the detection unit as to whether the water-intake cork is open or closed.

The UV light emitting unit includes a substrate mounted on the mounting unit and a UV light emitting device mounted on the substrate and emitting UV light towards the flow channel in the installation space, and the controller may control the UV light emitting device to be intermittently turned on.

The controller may control the UV light emitting device such that the UV light emitting device continues to be turned on while it is detected by the detection unit that the water-intake cork is open.

In accordance with a further embodiment of the disclosed technology, a sterilization module includes: a flow channel body including an inflow unit defining an inflow channel through which water flows in one direction, a discharge unit defining a discharge channel through which water is discharged in a direction parallel to the inflow channel, and a bypass channel unit having a bypass channel through which water bypasses in a different direction from the flow direction of water in the inflow unit; a UV light emitting unit emitting UV light towards the bypass channel; a mounting unit receiving the UV light emitting unit and formed on the flow channel body to connect an installation space to the bypass channel, the UV light emitting unit being disposed in the installation space; and a holder coupled to the mounting unit and securing the UV light emitting unit inside the mounting unit.

The bypass channel unit may include a first bypass channel unit connected to the inflow channel unit such that the inflow channel is connected to the bypass channel in a "⌐" shape; and a second bypass channel unit connected to the first bypass channel unit in a "⊓" shape and connected to the discharge unit such that the bypass channel is connected to the discharge channel in an "L" shape.

A joint between the first bypass channel unit and the second bypass channel unit may be formed with a penetrating portion and the mounting unit may be formed at the joint between the first bypass channel unit and the second bypass channel unit to protrude outward from flow channel body such that the installation space communicates with the penetrating portion.

The UV light emitting unit may include a substrate mounted on the mounting unit and a UV light emitting device mounted on the substrate and emitting UV light towards the bypass channel in the installation space.

The UV light emitting device may be disposed between the first bypass channel unit and the second bypass channel unit to emit UV light towards the bypass channel, and the first bypass channel unit may be connected to the second bypass channel unit such that the bypass channel can be exposed to UV light in a UV light radiation angle range of the UV light emitting device.

The sterilization module may further include a protective cover provided to the mounting unit to shield a space between the bypass channel and the UV light emitting device and formed of a UV light transmissive material.

The protective cover may include at least one of quartz, a poly(methyl methacrylate) resin, and a fluorine-based polymer resin having high UV light transmittance.

The sterilization module may further include a spacer disposed between the substrate and the protective cover to form a space between the UV light emitting device and the protective cover.

An inner protrusion may be formed between the flow channel body and the mounting unit to protrude into the mounting unit, and a sealing member may be disposed between the inner protrusion and the protective cover to seal a gap between the protective cover and the flow channel body.

The holder may be coupled to an inner peripheral surface of the mounting unit and compress the substrate towards the inner protrusion to secure the UV light emitting unit inside the mounting unit.

The sterilization module may further include a cable connected to the substrate to connect the substrate to a power supply, wherein the holder is formed with a cable hole through which the cable passes towards the substrate.

The UV light emitting device may emit UV light having a peak wavelength in the range of 200 nm to 280 nm.

The sterilization module may further include a reflector reflecting UV light emitted from the UV light emitting unit towards the bypass channel.

The reflector may be realized by aluminum or stainless steel on an inner peripheral surface of the flow channel body defining the bypass channel therein.

A pair of bypass channel units may be symmetrically disposed with respect to an imaginary straight line connecting the inflow channel to the discharge channel.

The sterilization module may further include at least one of an inflow side UV light emitting unit emitting UV light towards the inflow channel and the bypass channel and a discharge side UV light emitting unit emitting UV light towards the bypass channel and the discharge channel.

The inflow side UV light emitting unit or the discharge side UV light emitting unit may include a UV light emitting device disposed on an imaginary bisector bisecting an internal angle defined between the inflow channel and the discharge channel or between the bypass channel and the discharge channel to emit UV light towards the inflow channel and the bypass channel or towards the bypass channel and the discharge channel.

In accordance with yet another embodiment of the disclosed technology, a water purifier includes: a water reservoir storing purified water; a water pipe connected to the water reservoir; a water-intake cork opened or closed to allow selective discharge of water supplied through the water pipe; and the sterilization module disposed between the water pipe and the water-intake cork and sterilizing water flowing towards the water-intake cork through the water pipe.

The water purifier may further include: a detection unit detecting whether the water-intake cork is open or closed; and a controller controlling operation of the sterilization module depending upon a detection result of the detection unit as to whether the water-intake cork is open or closed.

The UV light emitting unit includes a substrate mounted on the mounting unit and a UV light emitting device mounted on the substrate and emitting UV light towards the bypass channel in the installation space, and the controller may control the UV light emitting device to be intermittently turned on.

The controller may control the UV light emitting device such that the UV light emitting device continues to be turned on while it is detected by the detection unit that the water-intake cork is open.

In accordance with yet another embodiment of the disclosed technology, a sterilization module includes: a main body open at upper and lower sides thereof; a protective cover disposed inside the main body to shield an interior of the main body from the outside and allowing UV light to pass therethrough; an inner holder disposed on the protective cover and fastened to an inner wall of the main body; a substrate secured to the inner wall of the main body by the inner holder; and a UV light emitting device emitting UV light towards the protective cover, wherein the inner holder includes a spacer disposed between the substrate and the protective cover to separate the UV light emitting device from the protective cover and a fixing holder disposed on the substrate and secured to the inner wall of the main body.

The sterilization module may further include a connector disposed on an upper or lower surface of the substrate and electrically connected to the substrate; and a cable detachably coupled to the connector, wherein one end of the cable is detachably coupled to the connector and the other end of the cable is placed outside after passing through the inner holder.

The main body may have a connection path defined therein to connect an upper space on the substrate to a lower space under the substrate.

When the connector is mounted on a lower surface of the substrate, the one end of the cable may be attached to the connector through the connection path.

The connector may be biased towards one side from the center of the substrate and the spacer may be open at one side thereof corresponding to the one side of the substrate toward which the connector is biased.

The fixing holder may include a depth adjusting portion protruding outward from an upper surface or an outer surface of the fixing holder and restricting a depth at which the fixing holder is coupled to the main body.

The inner holder may have an integral structure in which the spacer is integrally connected to the fixing holder.

The spacer may be formed with a substrate insertion groove receiving the substrate.

The inner holder may include a substrate seat protruding inward from an inner wall of the spacer to allow the substrate to be seated thereon and a substrate holding portion disposed on the substrate and fastened to an inner wall of the fixing holder.

The inner holder may have a structure in which the spacer is separated from the fixing holder, the substrate may be inserted between an upper surface of the spacer and a lower surface of the fixing holder, and the fixing holder may secure the substrate between the spacer and the fixing holder by compressing the substrate when the fixing holder is fastened to the main body.

The spacer may be formed with a displacement preventing portion protruding upward from an upper surface of the spacer and preventing the substrate from being displaced from a designated place, and the displacement preventing portion may have a height less than or equal to a thickness of the substrate.

The sterilization module may further include a cover seat formed at a lower portion of the main body and protruding inward from an inner surface of the main body such that the protective cover is seated on the cover seat, and an inner surface of the cover seat may have a tapered shape having a diameter gradually increasing towards a lower surface thereof.

The sterilization module may further include an inner sealing member disposed between an upper surface of the cover seat of the main body and a lower surface of the protective cover to seal a gap between the main body and the protective cover.

The UV light emitting device may emit UV light in the wavelength range of 200 nm to 280 nm.

The sterilization module may further include a body holding portion formed along an outer periphery of the main body and protruding from an outer surface of the main body.

The sterilization module may further include an outer holder fastened to an outer wall of the main body.

The sterilization module may further include an outer sealing member disposed between an upper surface of the body holding portion and a lower surface of the outer holder to seal a gap between the main body and the outer holder.

In accordance with yet another embodiment of the disclosed technology, a water purifier includes: a water reservoir storing water and at least one sterilization module disposed to pass through at least one surface of the water reservoir.

The sterilization module may further include a body holding portion formed along an outer periphery of the main body and protruding from an outer surface of the main body and an outer holder fastened to an outer wall of the main body, wherein an upper surface of the body holding portion contacts an inner surface of the water reservoir and a lower surface of the outer holder contacts an outer surface of the water reservoir.

A lower surface of the main body may be placed on a middle line of the water reservoir or below the middle line of the water reservoir.

In accordance with yet another embodiment of the disclosed technology, a system includes: a water purifier including a water reservoir storing water and at least one sterilization module disposed to pass through at least one surface of the water reservoir; and a water pipe connected to the water reservoir to allow the water stored in the water reservoir to flow therethrough.

The sterilization module may further include a body holding portion placed along an outer periphery of the main body and protruding from an outer surface of the main body and an outer holder fastened to an outer wall of the main body, wherein an upper surface of the body holding portion contacts an inner surface of the water reservoir and a lower surface of the outer holder contacts an outer surface of the water reservoir.

A lower surface of the main body may be placed on a middle line of the water reservoir or below the middle line of the water reservoir.

The system may further include a freezing device freezing water purified by the water purifier, wherein the freezing device includes a water purifier receiving the purified water through the water pipe.

The system may further include a humidification device converting water purified by the water purifier into water vapor, wherein the humidification device includes a water purifier receiving the purified water through the water pipe.

Embodiments of the disclosed technology provide a sterilization module capable of sterilizing water, a water purifier capable of storing and supplying purified water using the sterilization module, and a system including the water purifier.

Embodiments of the disclosed technology provide a sterilization module a self-assembled sterilization module, thereby allowing easy replacement of components or the sterilization module in a water purifier and a system including the water purifier.

DETAILED DESCRIPTION

Figure 1:
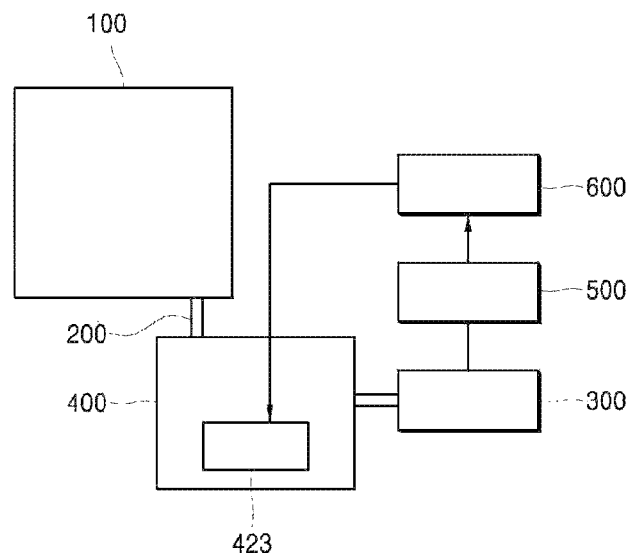
FIG. 1 is a block diagram of a water purifier according to one embodiment of the disclosed technology.

Hereinafter, embodiments of the disclosed technology will be described in detail with reference to the accompanying drawings. The following embodiments are provided by way of example so as to fully convey the spirit of the disclosed technology to those skilled in the art to which the disclosed technology pertains. Accordingly, the disclosed technology is not limited to the embodiments disclosed herein and can also be implemented in different forms. In the drawings, widths, lengths, thicknesses, and the like of elements can be exaggerated for clarity and descriptive purposes. Throughout the specification, like reference numerals denote like elements having the same or similar functions.

Figure 2:
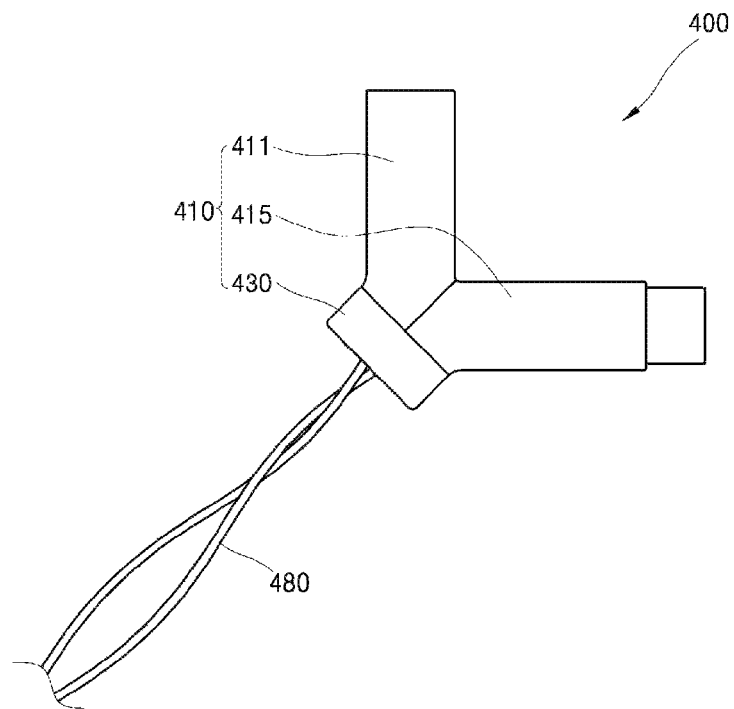
FIG. 2 is a front view of a sterilization module according to one embodiment of the disclosed technology.
Figure 3:
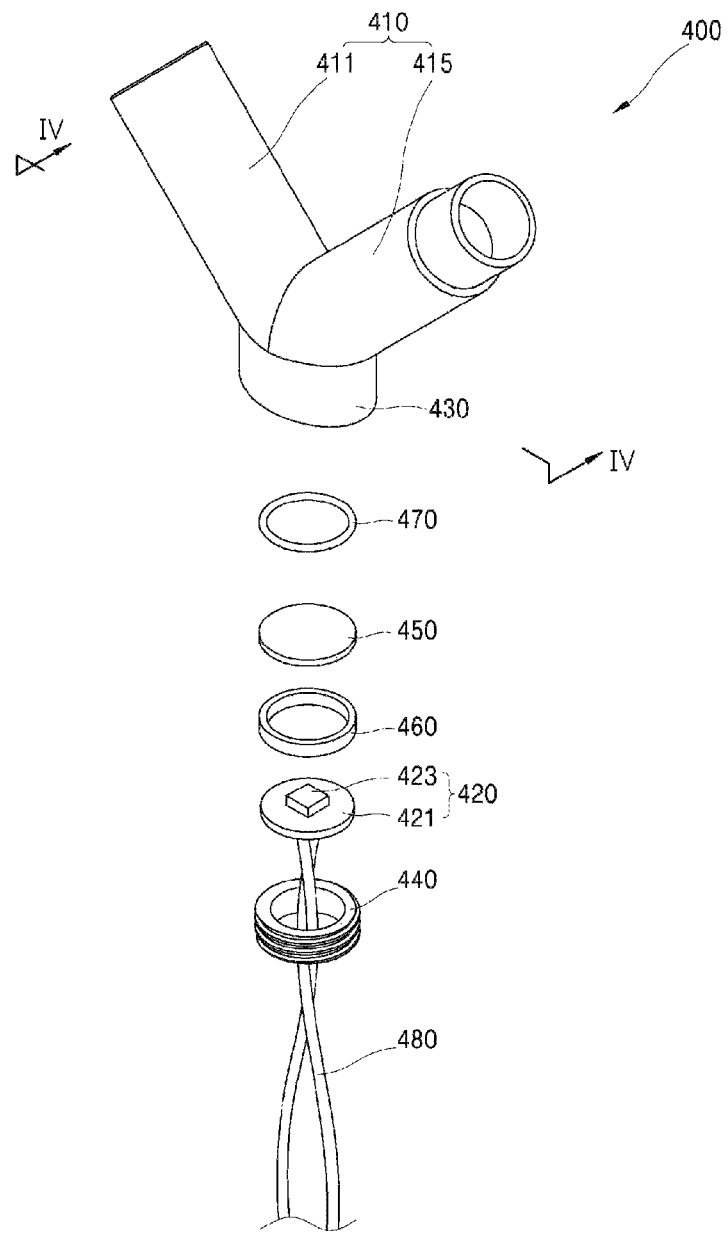
FIG. 3 is an exploded perspective view of the sterilization module shown in FIG. 2.
Figure 4:
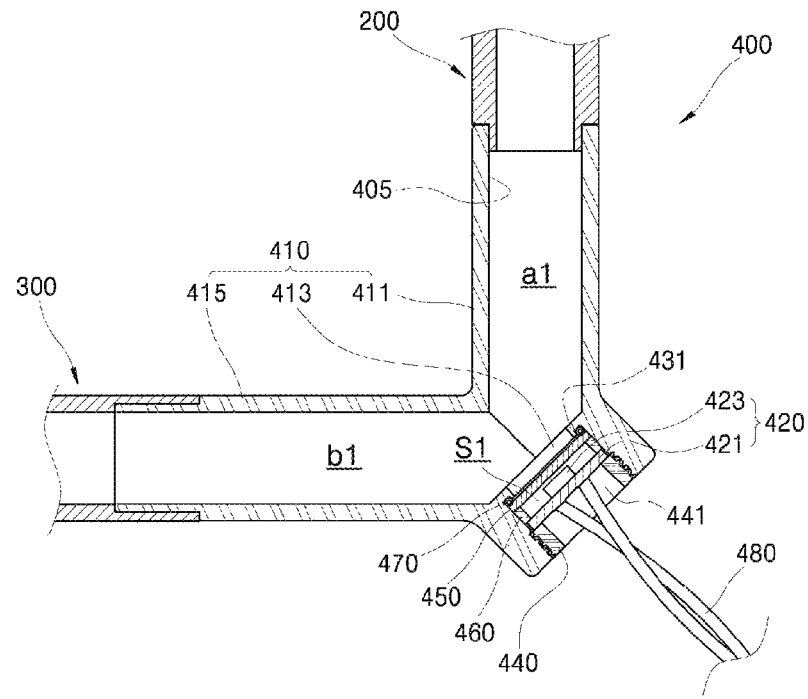
FIG. 4 is a cross-sectional view taken along line IV-IV of FIG. 2.

FIG. 1 is a block diagram of a water purifier according to one embodiment of the disclosed technology and FIG. 2 is a front view of a sterilization module according to one embodiment of the disclosed technology. FIG. 3 is an exploded perspective view of the sterilization module shown in FIG. 2 and FIG. 4 is a cross-sectional view taken along line IV-IV of FIG. 2.

Referring to FIG. 1 and FIG. 2, a water purifier according to one embodiment of the disclosed technology includes a water reservoir 100, a water pipe 200, a water-intake cork 300, and a sterilization module 400.

The water reservoir 100 is disposed in a main body (not shown) defining an outer appearance of the water purifier and stores purified water. Raw water supplied into the water purifier is purified by a filter disposed inside the main body, and water purified by the filter, that is, purified water, is stored in the water reservoir 100.

The water pipe 200 is disposed inside the main body and connected to the water reservoir 100. Water stored in the water reservoir 100 is supplied to the water-intake cork 300 through the water pipe 200.

The water-intake cork 300 is disposed outside the main body and is connected to the water pipe 200. The water-intake cork 300 is opened or closed to selectively discharge water supplied through the water pipe 200.

The sterilization module 400 is disposed between the water pipe 200 and the water-intake cork 300 inside the main body. The sterilization module 400 serves to sterilize water flowing towards the water-intake cork 300 through the water pipe 200 and includes a flow channel body 410, a UV light emitting unit 420, a mounting unit 430, and a holder 440, as shown in FIG. 3 and FIG. 4.

The flow channel body 410 defines an external appearance of the sterilization module 400 and has flow channels a1, b1 formed therein to allow water to pass therethrough. The flow channel body 410 may include an inflow unit 411 and a discharge unit 415.

The inflow unit 411 has a hollow pipe shape and is connected to the water pipe 200. According to this embodiment, the inflow unit 411 is press-fitted into the water pipe 200 such that the flow channel body 410 can be detachably coupled to the water pipe 200.

The inflow unit 411 has an inflow channel a1 through which water flows in one direction such that purified water supplied from the water pipe 200 can flow inside the inflow unit 411 through the inflow channel a1 in the inflow unit 411.

Like the inflow unit 411, the discharge unit 415 has a hollow pipe shape and is connected to the inflow unit 411. According to this embodiment, the discharge unit 415 is press-fitted into the water-intake cork 300 such that the flow channel body 410 can be detachably coupled to the water-intake cork 300.

The discharge channel b1 is formed in the discharge unit 415 and extends from the inflow channel a1 in a different direction from the inflow channel a1 to form the flow channels a1, b1 together with the inflow channel a1, such that purified water supplied from the water pipe 200 can flow towards the water-intake cork 300 through the discharge channel b1 in the discharge unit 415, after passing through the discharge unit 415.

According to this embodiment, the flow channel body 410 is formed in an "L" shape in which the inflow unit 411 is connected to the discharge unit 415 in an "L" shape. The flow channel body 410 can effectively connect the water pipe 200, which extends form the water reservoir 100 in the vertical direction, to an inlet port 310 of the water-intake cork 300, which extends from the water reservoir 100 in the horizontal direction.

A joint between the inflow unit 411 and the discharge unit 415 may be formed with a penetrating portion 413. The mounting unit 430 described below may be formed at the joint in which the penetrating portion 413 is formed.

The UV light emitting unit 420 may be disposed to emit UV light towards the flow channels a1, b1. The UV light emitting unit 420 is disposed inside the mounting unit 430.

The mounting unit 430 may have a hollow pipe shape so as to form an installation space s1 in which the UV light emitting unit 420 is disposed. Such a mounting unit 430 is formed on the flow channel body 410 such that the installation space s1 for installation of the UV light emitting unit 420 is connected to the flow channels a1, b1.

According to this embodiment, the mounting unit 430 is disposed at the joint between the inflow unit 411 and the discharge unit 415 and protrudes outward from the flow channel body 410 such that the installation space s1 defined in the mounting unit 430 communicates with the penetrating portion 413.

That is, the sterilization module 400 has a Y-shaped external appearance formed by connection between the inflow unit 411, the discharge unit 415 and the mounting unit 430.

Further, an inner protrusion 431 is formed between the flow channel body 410 and the mounting unit 430 and protrudes towards the mounting unit 430.

The inner protrusion 431 is formed at the penetrating portion 413, at which the installation space s1 is connected to the flow channels a1, b1, to protrude from an inner peripheral surface of the mounting unit 430 towards the center of the mounting unit 430, and serves to prevent the UV light emitting unit 420 mounted on the mounting unit 430 from being moved towards the flow channel body 410.

The holder 440 is coupled to the mounting unit 430 to hold the UV light emitting unit 420 inside the mounting unit 430.

In this embodiment, the holder 440 is provided in the form of a stopper covering the inner peripheral surface of the mounting unit 430 and coupled to the inner peripheral surface of the mounting unit 430 by screw coupling. Such a holder 440 serves to secure the UV light emitting unit 420 inside the mounting unit 430 by compressing a substrate 421 of the UV light emitting unit 420 described below towards the inner protrusion 431.

On the other hand, the UV light emitting unit 420 disposed inside the mounting unit 430 includes the substrate 421 mounted on the mounting unit 430 and a UV light emitting device 423 mounted on the substrate 421 to emit UV light towards the flow channels a1, b1.

The UV light emitting device 423 emits UV light, which has a peak wavelength of 200 nm to 280 nm, towards the flow channels a1, b1, and is disposed to allow UV light emitted from the UV light emitting device 423 to uniformly reach the flow channels a1, b1.

UV light having a peak wavelength of 270 nm to 280 nm, particularly, a peak wavelength of 275 nm, exhibits good sterilization effects.

According to this embodiment, the UV light emitting device 423 emits UV light having a peak wavelength of 275 nm, whereby sterilization can be actively performed in the flow channels a1, b1 through operation of the UV light emitting device 423.

However, in order to achieve effective sterilization, the UVC range, particularly, UV light having a peak wavelength of 250 nm to 280 nm may be used.

According to this embodiment, the UV light emitting device 423 is disposed on an imaginary bisector bisecting an internal angle defined between the inflow channel a1 and the discharge channel b1 and emits UV light towards the inflow channel a1 and the discharge channel b1.

In addition, the inflow unit 411 and the discharge unit 415 are connected to each other such that the inflow channel a1 and the discharge channel b1 can be exposed to UV light in a UV light radiation angle range of the UV light emitting device 423.

For example, when the UV light emitting device 423 emits UV light at an irradiation angle of 120°, the inflow unit 411 is connected to the discharge unit 415 such that an internal angle defined by the inflow channel a1 and the discharge channel b1 is 120° or less, preferably, 90°.

With this structure, the inflow channel a1 and the discharge channel b1 are exposed to UV light in the UV light radiation angle range of the UV light emitting device 423, whereby the entirety of the inflow channel a1 and the discharge channel b1 can be uniformly irradiated with UV light emitted from the UV light emitting device 423.

The mounting unit 430 may be further provided therein with a protective cover 450. The protective cover 450 is disposed inside the mounting unit 430, specifically between the penetrating portion 413 and the UV light emitting unit 420, to shield a space between the flow channels a1, b1 and the UV light emitting device 423.

In this structure, since the UV light emitting device 423 emits UV light towards the flow channels a1, b1 with the protective cover 450 disposed therebetween, the protective cover 450 is formed of a material allowing efficient transmission of UV light therethrough in order to allow UV light emitted from the UV light emitting device 423 to reach the flow channels a1, b1 such that sterilization can be efficiently achieved in the flow channels a1, b1.

Accordingly, the protective cover 450 may include at least one of quartz, a poly(methyl methacrylate) resin, and a fluorine-based polymer resin having high UV light transmittance.

Among these materials, quartz has excellent transmittance with respect to light substantially in all wavelength bands, and pure poly(methyl methacrylate) is mainly composed of carbon and hydrogen to form thin electron clouds, thereby providing high UV light transmittance. It could be seen that a poly(methyl methacrylate) resin having 85 wt % or more of an MMA monomer has high transmittance with respect to UV light.

In addition, the fluorine-based polymer resin is a copolymer obtained through copolymerization of tetrafluoroethylene and hexafluoropropylene, and exhibits high flexibility, high transmittance with respect to UV light, and is very resistant to UV light.

As such, according to this embodiment, the protective cover 450 includes at least one of quartz, the poly(methyl methacrylate) resin, and the fluorine-based polymer resin, whereby UV light emitted from the UV light emitting device 423 can be effectively reach the flow channels a1, b1 after passing through the protective cover 450.

Here, when the protective cover 450 is transparent, there can be a limitation in uniform irradiation of the flow channels a1, b1 with UV light emitted from the UV light emitting device 423, which is a spot light source.

Thus, according to this embodiment, an inner or outer surface of the protective cover 450 is subjected to roughening such that UV light emitted from the spot light source can be spread or scattered while passing through the protective cover 450, thereby providing sheet light.

The inner or outer surface of the protective cover 450 may be subjected to sand blasting to form a roughened surface. Particularly, when the protective cover 450 is formed of a poly(methyl methacrylate) resin, the protective cover 450 having a roughened inner or outer surface may be fabricated by sand-blasting the inner or outer surface of the protective cover 450 after injection, or may be fabricated by injection molding using an inner or outer surface of a mold, which is subjected to sand blasting.

The mounting unit 430 may be further provided with a spacer 460 therein. The spacer 460 is disposed between the substrate 421 and the protective cover 450 and forms a space between the UV light emitting device 423 and the protective cover 450 so as to secure a space for installation of the UV light emitting device 423.

The mounting unit 430 may be further provided with a sealing member 470 therein. The sealing member 470 is disposed between the inner protrusion 431 and the protective cover 450 and seals a gap between the protective cover 450 and the flow channel body 410 to prevent water flowing inside the flow channel body 410 from entering the mounting unit 430.

According to this embodiment, the components of the sterilization module 400 are assembled in the sequence of the sealing member 470, the protective cover 450, the spacer 460, and the UV light emitting unit 420 on the inner protrusion 431 inside the mounting unit 430.

Then, the holder 440 compresses the substrate 421 towards the inner protrusion upon screw coupling of the holder 440 to the inner peripheral surface of the mounting unit 430, so that the components of the sterilization module including the UV light emitting unit 420 are secured inside the mounting unit 430, and the sealing member 470 is brought into close contact with the inner protrusion 431 and the protective cover 450 to seal a gap between the protective cover 450 and the flow channel body 410.

The UV light emitting unit 420 disposed inside the mounting unit 430 may receive electric power through a cable 480.

According to this embodiment, the UV light emitting unit 420 may be connected to a power supply (not shown) through connection between the substrate 421 and the cable 480 and the holder 440 may be formed with a cable hole 441 through which the cable 480 extending from the power source is connected to the substrate 421.

The sterilization module 400 according to this embodiment may further include a reflector 405 disposed to reflect UV light emitted from the UV light emitting unit 420 towards the flow channels a1, b1.

According to this embodiment, the reflector 405 may be formed of aluminum or stainless steel having high reflectance with respect to UV light on an inner peripheral surface of the flow channel body 410, which define the flow channels a1, b1 therein.

Since the flow channel body 410 is formed of aluminum or stainless steel, the reflector 405 may be constituted by the inner peripheral surface of the flow channel body 410, or may be formed by coating the inner peripheral surface of the flow channel body 410 with aluminum. Alternatively, other materials having high reflectance with respect to UV light may be used as the material of the flow channel body 410 or as the coating material.

The reflector 405 enlarges or increases a UV-irradiated region and a UV irradiation time by reflecting UV light, which is emitted from the UV light emitting unit 420, towards the flow channels a1, b1 inside the flow channel body 410, thereby enabling more efficient sterilization in the flow channels a1, b1 through irradiation with UV light.

As shown in FIG. 1 and FIG. 4, the water purifier according to this embodiment may further include a detection unit 500 and a controller 600.

The detection unit 500 is disposed to detect whether the water-intake cork 300 is open or closed. The detection unit 500 may be realized in the form of a sensor detecting a manipulation switch (not shown) to manipulate opening or closing of the water-intake cork 300 or in the form of a sensor detecting discharge of water through the water-intake cork 300.

The controller 600 may control the sterilization module 400 depending upon a detection result of the detection unit 500 as to whether the water-intake cork 300 is open or closed.

The controller 600 may control the UV light emitting device 423 to be intermittently turned on, that is, to be repeatedly turned on and turned off with predetermined time intervals, when the water-intake cork 300 is in a closed state, that is, in a state wherein discharge of water through the water-intake cork 300 is not performed.

In addition, the controller 600 may control the UV light emitting device 423 such that the UV light emitting device 423 continues to be turned on while it is detected by the detection unit 500 that the water-intake cork 300 is open, that is, in a state wherein discharge of water through the water-intake cork 300 is performed.

Figure 5:
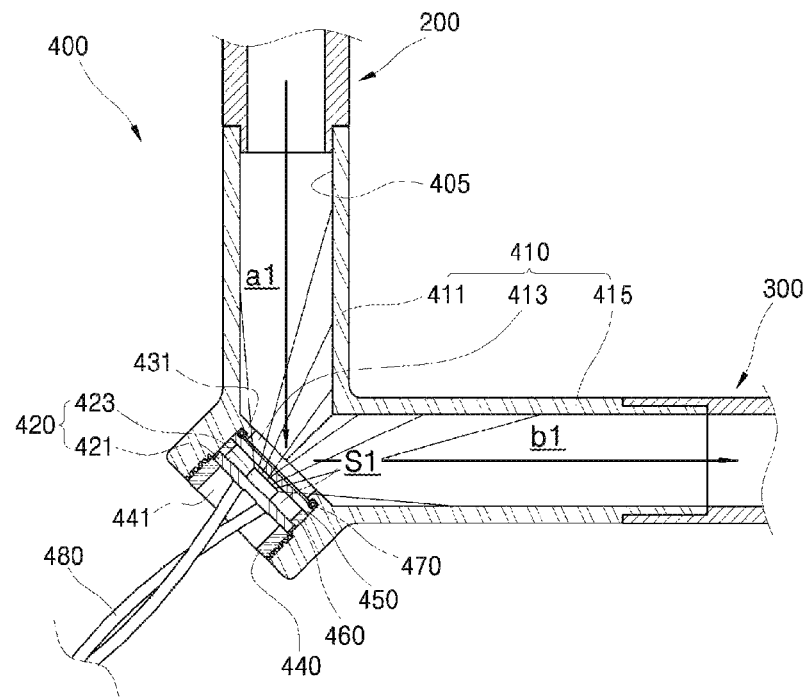
FIG. 5 is a cross-sectional view of the sterilization module according to the embodiment of the disclosed technology upon sterilization of water.

FIG. 5 is a cross-sectional view of the sterilization module according to the embodiment of the disclosed technology upon sterilization of water.

Next, operation and effects of the water purifier including the sterilization module according to this embodiment will be described with reference to FIG. 1 and FIG. 5.

Referring to FIG. 1 and FIG. 5, the sterilization module 400 is disposed between the water pipe 200 connected to the water reservoir 100 and the water-intake cork 300 to be detachably coupled to the water pipe 200 and the water-intake cork 300.

As such, since connection and separation of the sterilization module 400 can be easily performed, the sterilization module 400 can be easily and rapidly coupled to the water purifier, thereby enabling reduction in cost and time for maintenance operation such as repair, replacement, and the like.

Since installation of the sterilization module 400 can be completed simply by fitting the sterilization module 400 between the water pipe 200 and the water-intake cork 300, the sterilization module 400 according to this embodiment can be easily applied to a typical water purifier having a structure in which a water reservoir is connected to a water-intake cork by a water pipe.

In the structure wherein the sterilization module 400 is disposed between the water pipe 200 and the water-intake cork 300, purified water stored in the water reservoir 100 can be supplied to the sterilization module 400, that is, to the flow channels a1, b1, through the water pipe 200. Then, the water supplied to the flow channels a1, b1 can be supplied towards the water-intake cork 300 after passing through the flow channels a1, b1.

In this state, when the UV light emitting device 121 is turned on, the UV light emitting device 121 emits UV light having high sterilization effects, for example, UV light having a peak wavelength of 200 nm to 280 nm, preferably, UV light having a peak wavelength of 275 nm, towards the flow channels a1, b1.

As such, since UV light having high sterilization effects is emitted towards the flow channels a1, b1, the interior of the flow channel body 410, which defines the flow channels a1, b1, and water flowing through the flow channels a1, b1 can be sterilized thereby.

As a result, it is possible to supply purified water to the water-intake cork 300 after removing and sterilizing microorganisms, bacteria, and the like in the water supplied through the water reservoir 100 and the water pipe 200.

Particularly, the UV light emitting device 423 is disposed at a bent portion, at which the flow channels a1, b1 are connected to each other in an "L" shape, and emits UV light in the same direction as the flow channels a1, b1, so that water flowing through the flow channels a1, b1 can be exposed to UV light for a long period of time, thereby further improving sterilization effects.

The time and interval for such a sterilization process can be regulated through control of the sterilization module by the controller 600.

That is, in a state wherein the water-intake cork 300 is closed to allow water to remain in the flow channels a1, b1, the UV light emitting device 423 is controlled to be intermittently turned on, thereby enabling intermittent sterilization so as to suppress proliferation of microorganisms and bacteria in the flow channels a1, b1.

Further, in a state wherein the water-intake cork 300 is opened to allow water to be discharged through the water-intake cork 300, the UV light emitting device 423 is controlled to be turned on, thereby enabling sterilization so as to allow water passing through the flow channels a1, b1 to be discharged through the water-intake cork 300 after being sterilized.

Advantageously, the sterilization module 400 according to this embodiment and the water purifier including the same can supply clean water subjected to sterilization immediately before water intake by effectively sterilizing microorganisms and bacteria contained in water supplied from the water reservoir 100 through the water pipe 200 while effectively suppressing proliferation of the microorganisms and the bacteria in the water purifier.

In addition, since installation of the sterilization module 400 according to this embodiment can be completed simply by fitting the sterilization module 400 between the water pipe 200 and the water-intake cork 300, the sterilization module 400 according to this embodiment can be easily applied to a typical water purifier having a structure in which a water reservoir is connected to a water-intake cork by a water pipe.

Figure 6:
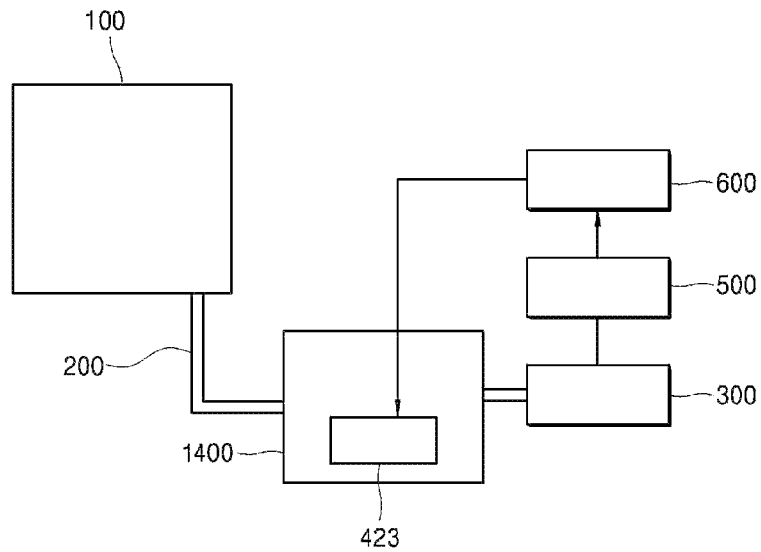
FIG. 6 is a block diagram of a water purifier according to another embodiment of the disclosed technology.
Figure 7:
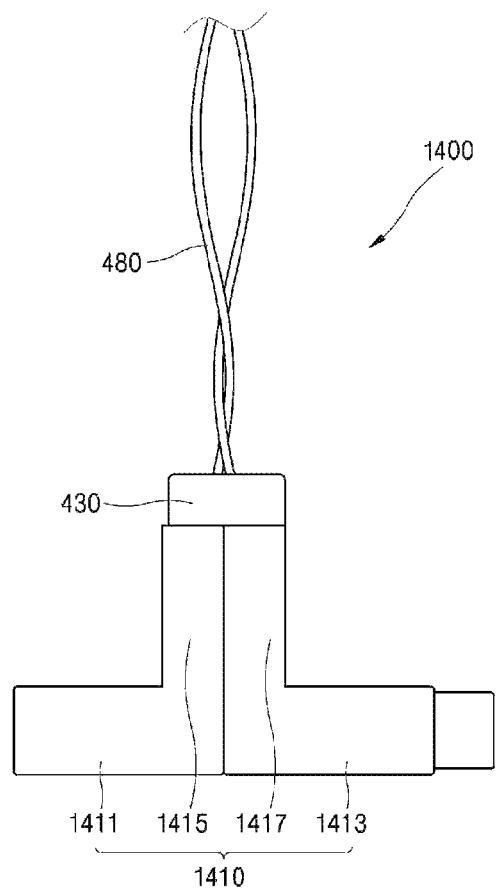
FIG. 7 is a front view of a sterilization module according to another embodiment of the disclosed technology.
Figure 8:
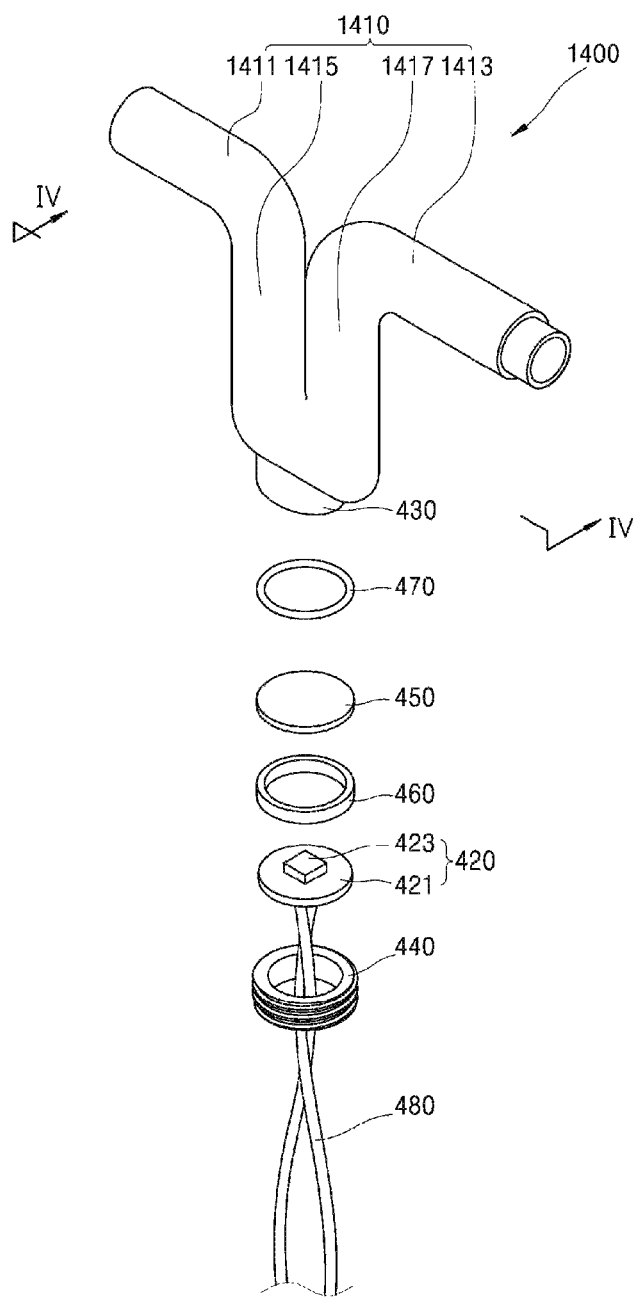
FIG. 8 is an exploded perspective view of the sterilization module shown in FIG. 7.
Figure 9:
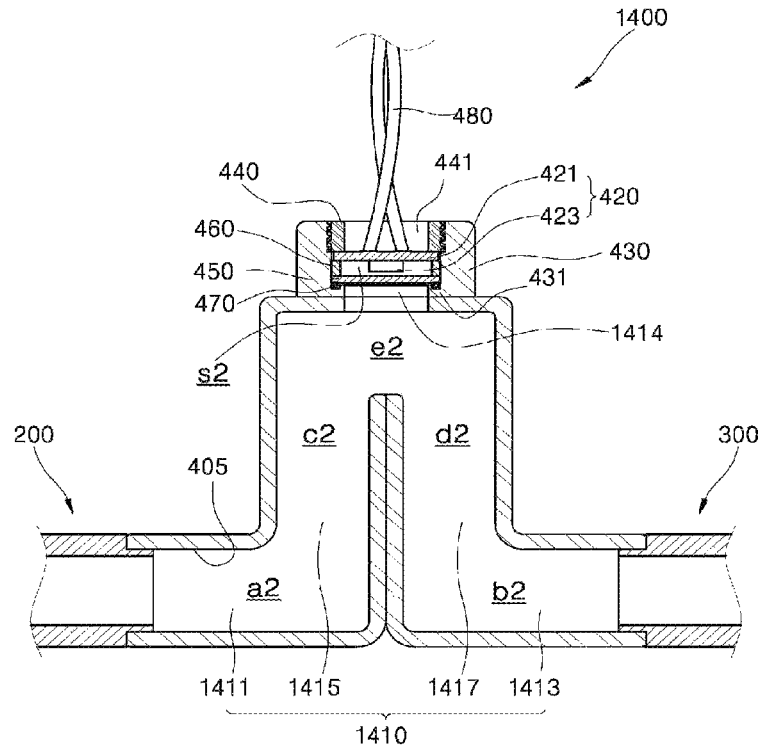
FIG. 9 is a cross-sectional view taken along line IV-IV of FIG. 7.

FIG. 6 is a block diagram of a water purifier according to another embodiment of the disclosed technology and FIG. 7 is a front view of a sterilization module according to another embodiment of the disclosed technology. FIG. 8 is an exploded perspective view of the sterilization module shown in FIG. 7 and FIG. 9 is a cross-sectional view taken along line IV-IV of FIG. 7.

Referring to FIG. 6 and FIG. 7, a water purifier according to another embodiment of the disclosed technology includes a water reservoir 100, a water pipe 200, a water-intake cork 300, and a sterilization module 1400.

The water reservoir 100 is disposed in a main body (not shown) defining an outer appearance of the water purifier and stores purified water. Raw water supplied into the water purifier is purified by a filter disposed inside the main body, and water purified by the filter, that is, purified water, is stored in the water reservoir 100.

The water pipe 200 is disposed inside the main body and connected to the water reservoir 100. Water stored in the water reservoir 100 is supplied to the water-intake cork 300 through the water pipe 200.

The water-intake cork 300 is disposed outside the main body and connected to the water pipe 200. The water-intake cork 300 is opened or closed to selectively discharge water supplied through the water pipe 200.

According to this embodiment, the water pipe 200 is connected to the water-intake cork 300 to form a straight flow channel, with the sterilization module 1400 interposed therebetween.

The sterilization module 1400 is disposed between the water pipe 200 and the water-intake cork 300 inside the main body. The sterilization module 1400 serves to sterilize water flowing towards the water-intake cork 300 through the water pipe 200 and includes a flow channel body 1410, a UV light emitting unit 420, a mounting unit 430, and a holder 440, as shown in FIG. 8 and FIG. 9.

The flow channel body 1410 defines an external appearance of the sterilization module 1400 and includes an inflow unit 1411, a discharge unit 1413, and bypass channel units 1415, 1417.

The inflow unit 1411 has a hollow pipe shape and is connected to the water pipe 200. According to this embodiment, the inflow unit 4111 is press-fitted into the water pipe 200 such that the flow channel body 1410 can be detachably coupled to the water pipe 200.

The inflow unit 1411 is connected to a discharge side of the water pipe 200 to form a straight-line structure. Such an inflow unit 1411 has an inflow channel a2 which receives water from the water pipe 200 in one direction.

Like the inflow unit 1411, the discharge unit 1413 has a hollow pipe shape and is connected to the inflow unit of the water-intake cork 300. According to this embodiment, the discharge unit 1413 is press-fitted into the water-intake cork 300 such that the flow channel body 1410 can be detachably coupled to the water-intake cork 300.

The discharge unit 1413 is connected to an inlet side of the water-intake cork 300 to form a straight-line structure. Such a discharge unit 1413 has a discharge channel b2 through which water is discharged in a direction parallel to the inflow channel a2 and the inlet side of the water-intake cork 300.

The bypass channel units 1415, 1417 are formed between the inflow unit 1411 and the discharge unit 1413. The bypass channel units 1415, 1417 have bypass channels c2, d2, e2 through which water is bypassed in a different direction from the inflow unit 1411 and the discharge unit 1413.

According to this embodiment, the bypass channel units 1415, 1417 include a first bypass channel unit 1415 and a second bypass channel unit 1417.

The first bypass channel unit 1415 is connected to the inflow unit 1411 such that the inflow channel a2 is connected to the bypass channel c2 in a "⌐" shape.

The second bypass channel unit 1417 is connected to the discharge unit 1413 such that the second bypass channel unit 1417 is connected to the first bypass channel unit 1415 in a "⊓" shape and the bypass channel e2 is connected to the discharge channel b2 in an "L" shape.

Among the bypass channels c2, d2, e2 formed in the first bypass channel unit 1415 and the second bypass channel unit 1417 connected to each other, the bypass channel c2 formed in the first bypass channel unit 1415 is connected to the inflow channel a2 in a "⌐" shape, the bypass channel e2 formed in the second bypass channel unit 1417 is connected to the discharge channel b2 in a "⌐" shape, and the bypass channel d2 connects the first bypass channel unit 1415 to the second bypass channel unit 1417 in a "⊓" shape.

The bypass channel units 1415, 1417 formed to have the bypass channels c2, d2, e2 therein increases the time for which water sterilization by the sterilization module 1400 is applied to water passing through the sterilization module 1400 by increasing the flow distance and time of water passing through the sterilization module 1400.

In the flow channel body 1410 with the structure as described above, the inflow unit 1411 and the discharge unit 1413 respectively connected to opposite ends of the bypass channel units 1415, 1417 are arranged in a straight-line structure and thus can effectively connect the water pipe 200 to the water-intake cork 300 arranged in a straight-line structure.

Advantageously, the sterilization module 1400 including the flow channel body 1410 according to this embodiment can be easily applied to a typical water purifier in which the water pipe 200 and the water-intake cork 300 are arranged in a straight-line structure.

Furthermore, a joint between the first bypass channel unit 1415 and the second bypass channel unit 1417 may be formed with a penetrating portion 414. The mounting unit 430 described below may be formed at the joint in which the penetrating portion 414 is formed.

The UV light emitting unit 420 is disposed to emit UV light towards the bypass channels c2, d2, e2. The UV light emitting unit 420 is disposed inside the mounting unit 430.

The mounting unit 430 has a hollow pipe shape so as to form an installation space s2 in which the UV light emitting unit 420 is disposed. The mounting unit 430 is formed on the flow channel body 1410 such that the installation space s2 for installation of the UV light emitting unit 420 is connected to the bypass channels c2, d2, e2.

According to this embodiment, the mounting unit 430 is disposed at the joint between the first bypass channel unit 1415 and the second bypass channel unit 1417 and protrudes outward from the flow channel body 1410 such that the installation space s2 defined in the mounting unit 430 communicates with the penetrating portion 414.

Further, an inner protrusion 431 is formed between the flow channel body 1410 and the mounting unit 430 and protrudes towards the mounting unit 430.

The inner protrusion 431 is formed at the penetrating portion 414, at which the installation space s2 is connected to the bypass channels c2, d2, e2, to protrude from an inner peripheral surface of the mounting unit 430 towards the center of the mounting unit 430, and serves to prevent the UV light emitting unit 420 mounted on the mounting unit 430 from being moved towards the flow channel body 1410.

The holder 440 is coupled to the mounting unit 430 to hold the UV light emitting unit 420 inside the mounting unit 430.

In this embodiment, the holder 440 is provided in the form of a stopper covering the inner peripheral surface of the mounting unit 430 and screw-coupled to the inner peripheral surface of the mounting unit 430. Such a holder 440 serves to secure the UV light emitting unit 420 inside the mounting unit 430 by compressing a substrate 421 of the UV light emitting unit 420 described below towards the inner protrusion 431.

On the other hand, the UV light emitting unit 420 disposed inside the mounting unit 430 includes the substrate 421 mounted on the mounting unit 430 and a UV light emitting device 423 mounted on the substrate 421 to emit UV light towards the bypass channels c2, d2, e2.

The UV light emitting device 423 emits UV light, which has a peak wavelength of 200 nm to 280 nm, towards the bypass channels c2, d2, e2, and is disposed to allow UV light emitted from the UV light emitting device 423 to uniformly reach the bypass channels c2, d2, e2.

UV light having a peak wavelength of 200 nm to 280 nm, particularly, a peak wavelength of 275 nm, exhibits good sterilization effects.

According to this embodiment, the UV light emitting device 423 emits UV light having a peak wavelength of 275 nm, whereby sterilization can be actively performed in the bypass channels c2, d2, e2 through operation of the UV light emitting device 423.

However, in order to achieve effective sterilization, the UVC range, particularly, UV light having a peak wavelength of 250 nm to 280 nm may be used.

According to this embodiment, the UV light emitting device 423 is disposed between the first bypass channel unit 1415 and the second bypass channel unit 1417 and emits UV light towards the bypass channels c2, d2, e2.

In addition, the first bypass channel unit 1415 and the second bypass channel unit 1417 are connected to each other such that the bypass channels c2, d2, e2 can be exposed to UV light in a UV light radiation angle range of the UV light emitting device 423.

With this structure, the bypass channels c2, d2, e2 are exposed to UV light in the UV light radiation angle range of the UV light emitting device 423, whereby the entirety of the bypass channels c2, d2, e2 can be uniformly irradiated with UV light emitted from the UV light emitting device 423.

The mounting unit 430 may be further provided therein with a protective cover 450. The protective cover 450 is disposed inside the mounting unit 430, specifically between the penetrating portion 414 and the UV light emitting unit 420, to shield a space between the bypass channels c2, d2, e2 and the UV light emitting device 423.

In this structure, since the UV light emitting device 423 emits UV light towards the bypass channels c2, d2, e2 with the protective cover 450 disposed therebetween, the protective cover 450 is formed of a material allowing efficient transmission of UV light therethrough in order to allow UV light emitted from the UV light emitting device 423 to reach the bypass channels c2, d2, e2 such that sterilization can be efficiently achieved in the bypass channels c2, d2, e2.

Accordingly, the protective cover 450 may include at least one of quartz, a poly(methyl methacrylate) resin, and a fluorine-based polymer resin having high UV light transmittance.

Among these materials, quartz has excellent transmittance with respect to light substantially in all wavelength bands, and pure poly(methyl methacrylate) is mainly composed of carbon and hydrogen to form thin electron clouds, thereby providing high UV light transmittance. It could be seen that a poly(methyl methacrylate) resin having 85 wt % or more of an MMA monomer has high transmittance with respect to UV light.

In addition, the fluorine-based polymer resin is a copolymer obtained through copolymerization of tetrafluoroethylene and hexafluoropropylene, and exhibits high flexibility, high transmittance with respect to UV light, and is very resistant to UV light.

As such, according to this embodiment, the protective cover 450 includes at least one of quartz, the poly(methyl methacrylate) resin, and the fluorine-based polymer resin, whereby UV light emitted from the UV light emitting device 423 can be effectively reach the bypass channels c2, d2, e2 after passing through the protective cover 450.

Here, when the protective cover 450 is transparent, there can be a limitation in uniform irradiation of the bypass channels c2, d2, e2 with UV light emitted from the UV light emitting device 423, which is a spot light source.

Thus, according to this embodiment, an inner or outer surface of the protective cover 450 is subjected to roughening such that UV light emitted from the spot light source can be spread or scattered while passing through the protective cover 450, thereby providing sheet light.

The inner or outer surface of the protective cover 450 may be subjected to sand blasting to form a roughened surface. Particularly, when the protective cover 450 is formed of a poly(methyl methacrylate) resin, the protective cover 450 having a roughened inner or outer surface may be fabricated by sand-blasting the inner or outer surface of the protective cover 450 after injection molding, or may be fabricated by injection molding using an inner or outer surface of a mold, which is subjected to sand blasting.

The mounting unit 430 may be further provided with a spacer 460 therein. The spacer 460 is disposed between the substrate 421 and the protective cover 450 and forms a space between the UV light emitting device 423 and the protective cover 450 so as to secure a space for installation of the UV light emitting device 423.

The mounting unit 430 may be further provided with a sealing member 470 therein. The sealing member 470 is disposed between the inner protrusion 431 and the protective cover 450 and seals a gap between the protective cover 450 and the flow channel body 1410 to prevent water flowing inside the flow channel body 1410 from entering the mounting unit 430.

According to this embodiment, the components of the sterilization module 400 are assembled in the sequence of the sealing member 470, the protective cover 450, the spacer 460, and the UV light emitting unit 420 on the inner protrusion 431 inside the mounting unit 430.

Then, the holder 440 compresses the substrate 421 towards the inner protrusion upon screw coupling of the holder 440 to the inner peripheral surface of the mounting unit 430, so that the components of the sterilization module including the UV light emitting unit 420 are secured inside the mounting unit 430, and the sealing member 470 is brought into close contact with the inner protrusion 431 and the protective cover 450 to seal a gap between the protective cover 450 and the flow channel body 1410.

The UV light emitting unit 420 disposed inside the mounting unit 430 may receive electric power through a cable 480.

According to this embodiment, the UV light emitting unit 420 may be connected to a power supply (not shown) through connection between the substrate 421 and the cable 480 and the holder 440 may be formed with a cable hole 441 through which the cable 480 extending from the power source is connected to the substrate 421.

The sterilization module 400 according to this embodiment may further include a reflector 405 disposed to reflect UV light emitted from the UV light emitting unit 420 towards the bypass channels c2, d2, e2 and towards the inflow channel a2 and the discharge channel b2.

According to this embodiment, the reflector 405 may be formed of aluminum or stainless steel having high reflectance with respect to UV light on an inner peripheral surface of the flow channel body 1410, which defines the inflow channel a2, the discharge channel b2 and the bypass channels c2, d2, e2.

Since the flow channel body 1410 is formed of aluminum or stainless steel, the reflector 405 may be constituted by the inner peripheral surface of the flow channel body 1410, or may be formed by coating the inner peripheral surface of the flow channel body 1410 with aluminum. Alternatively, other materials having high reflectance with respect to UV light may be used as the material of the flow channel body 1410 or as the coating material.

The reflector 405 enlarges or increases a UV-irradiated region and a UV irradiation time by reflecting UV light, which is emitted from the UV light emitting unit 420, towards the flow channels a2, b2, c2, d2, e2 inside the flow channel body 1410, thereby enabling more efficient sterilization in the flow channels a2, b2, c2, d2, e2 through irradiation with UV light.

As shown in FIG. 6, the water purifier according to this embodiment may further include a detection unit 500 and a controller 600.

The detection unit 500 is disposed to detect whether the water-intake cork 300 is open or closed. The detection unit 500 may be realized in the form of a sensor detecting a manipulation switch (not shown) to manipulate opening or closing of the water-intake cork 300 or in the form of a sensor detecting discharge of water through the water-intake cork 300.

The controller 600 may control the sterilization module 400 depending upon a detection result of the detection unit 500 as to whether the water-intake cork 300 is open or closed.

The controller 600 may control the UV light emitting device 423 to be intermittently turned on, that is, to be repeatedly turned on and turned off with time intervals, when the water-intake cork 300 is in a closed state, that is, in a state wherein discharge of water through the water-intake cork 300 is not performed.

In addition, the controller 600 may control the UV light emitting device 423 such that the UV light emitting device 423 continues to be turned on while it is detected by the detection unit 500 that the water-intake cork 300 is open, that is, in a state wherein discharge of water through the water-intake cork 300 is performed.

Figure 10:
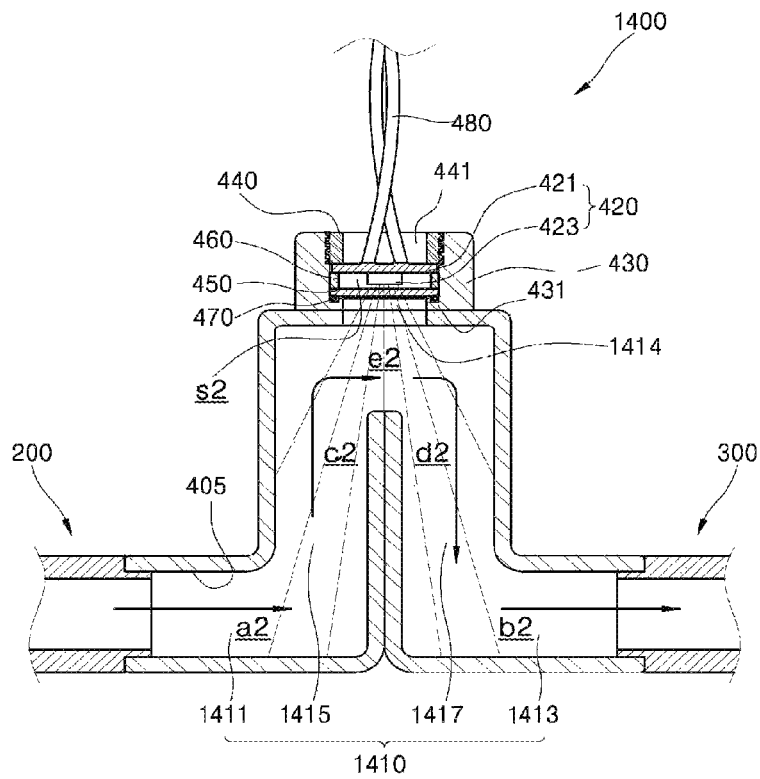
FIG. 10 is a cross-sectional view of the sterilization module according to the embodiment of the disclosed technology upon sterilization of water.

FIG. 10 is a cross-sectional view of the sterilization module according to this embodiment of the disclosed technology upon sterilization of water.

Next, operation and effects of the water purifier including the sterilization module according to this embodiment will be described with reference to FIG. 6 and FIG. 10.

Referring to FIG. 6 and FIG. 10, the sterilization module 1400 is disposed between the water pipe 200 connected to the water reservoir 100 and the water-intake cork 300 to be detachably coupled to the water pipe 200 and the water-intake cork 300.

As such, since connection and separation of the sterilization module 1400 can be easily performed, the sterilization module 1400 can be easily and rapidly coupled to the water purifier, thereby enabling reduction in cost and time for maintenance operation such as repair, replacement, and the like.

Since installation of the sterilization module 1400 can be completed simply by fitting the sterilization module 1400 between the water pipe 200 and the water-intake cork 300, the sterilization module 1400 according to this embodiment can be easily applied to a typical water purifier having a structure in which a water reservoir is connected to a water-intake cork by a water pipe.

In the structure wherein the sterilization module 400 is disposed between the water pipe 200 and the water-intake cork 300, purified water stored in the water reservoir 100 can be supplied to the sterilization module 400, that is, to the flow channels a2, b2, c2, d2, e2, through the water pipe 200. Then, the water supplied to the flow channels a2, b2, c2, d2, e2 can be supplied towards the water-intake cork 300 after passing through the flow channels a2, b2, c2, d2, e2.

In this state, when the UV light emitting device 121 is turned on, the UV light emitting device 121 emits UV light having high sterilization effects, for example, UV light having a peak wavelength of 200 nm to 280 nm, preferably, UV light having a peak wavelength of 275 nm, towards the flow channels a2, b2, c2, d2, e2, specifically the bypass channels c2, d2, e2.

As such, since UV light having high sterilization effects is emitted towards the bypass channels c2, d2, e2, the interior of the flow channel body 410, which defines the bypass channels c2, d2, e2, and water flowing through the bypass channels c2, d2, e2 can be sterilized thereby.

As a result, it is possible to supply purified water to the water-intake cork 300 after removing and sterilizing microorganisms, bacteria, and the like from the water supplied through the water reservoir 100 and the water pipe 200.

As such, the bypass channels c2, d2, e2 formed in the bypass channel units 1415, 1417 increase the flow distance and time of water passing through the sterilization module 1400, so that water flowing through the flow channels a2, b2, c2, d2, e2 can be exposed to UV light for a long period of time, thereby further improving sterilization effects.

In addition, the UV light emitting device 423 is disposed at the joint between the first bypass channel unit 1415 and the second bypass channel unit 1417 connected to each other in a "¬" shape, and emits UV light in the same direction as the bypass channels c2, e2, so that water flowing through the bypass channels c2, e2 can be exposed to UV light for a long period of time, thereby further improving the sterilization effects.

The time and interval for such a sterilization process can be regulated through control of the sterilization module by the controller 600.

That is, in a state wherein the water-intake cork 300 is closed to allow water to remain in the flow channels a2, b2, c2, d2, e2, the UV light emitting device 423 is controlled to be intermittently turned on, thereby enabling intermittent sterilization so as to suppress proliferation of microorganisms and bacteria in the flow channels a2, b2, c2, d2, e2.

Further, in a state wherein the water-intake cork 300 is opened to allow water to be discharged through the water-intake cork 300, the UV light emitting device 423 is controlled to be turned on, thereby enabling sterilization so as to allow water passing through the flow channels a2, b2, c2, d2, e2 to be discharged through the water-intake cork 300 after being sterilized.

Advantageously, the sterilization module 400 according to this embodiment and the water purifier including the same can supply clean water subjected to sterilization immediately before water intake by effectively sterilizing microorganisms and bacteria contained in water supplied from the water reservoir 100 through the water pipe 200 while effectively suppressing proliferation of the microorganisms and the bacteria in the water purifier.

In addition, the sterilization module 1400 according to this embodiment can increase the flow distance and time of water passing through the bypass channels c2, d2, e2 in the sterilization module 1400 and allows UV light to be emitted in the same direction as the bypass channels c2, e2, thereby further improving water sterilization effects through irradiation with UV light by increasing the time for which water is exposed to UV light.

Further, since installation of the sterilization module 400 according to this embodiment can be completed simply by fitting the sterilization module 400 between the water pipe 200 and the water-intake cork 300, the sterilization module 400 according to this embodiment can be easily applied to a typical water purifier having a structure in which a water reservoir is connected to a water-intake cork by a water pipe.

On the other hand, it should be understood that the sterilization modules and the water purifiers including the same according to the embodiments of the invention are provided for illustration only and various modifications can be made without departing from the scope of the disclosed technology.

Figure 11:
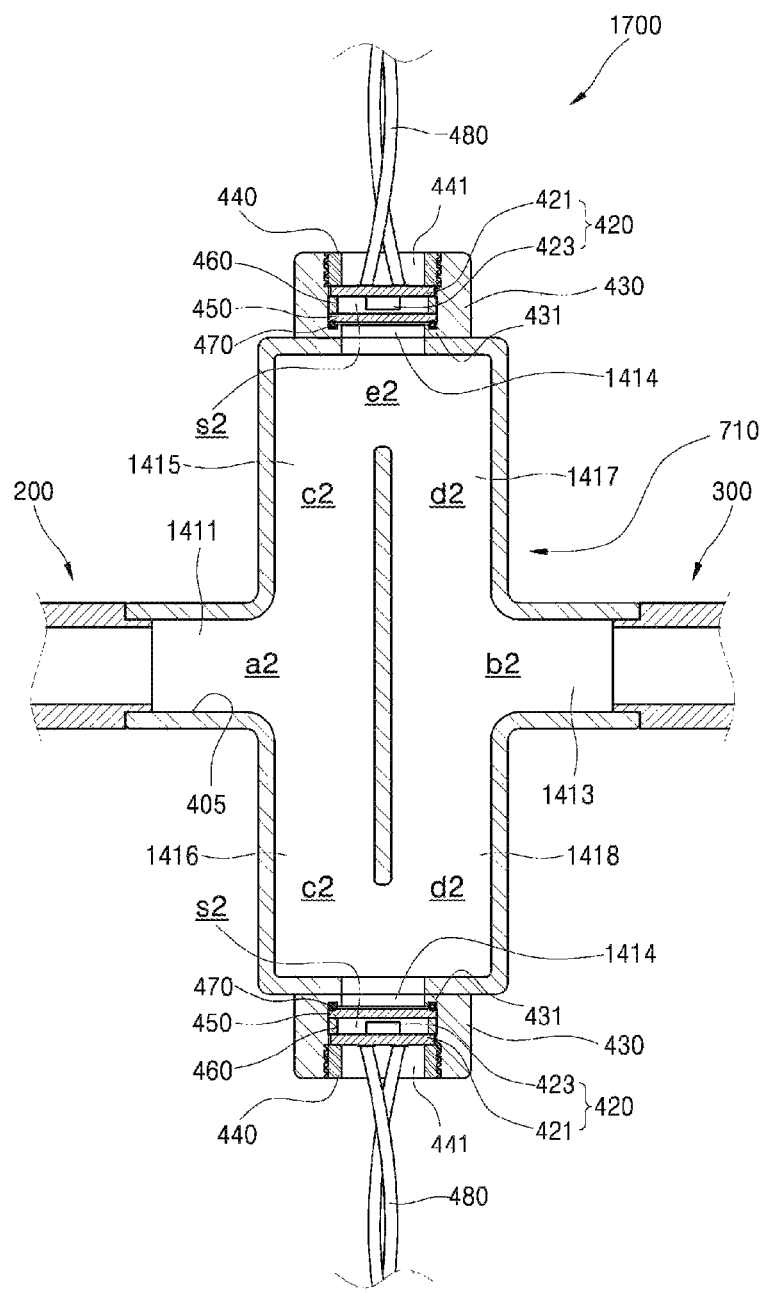
FIG. 11 is a cross-sectional view of a sterilization module according to a further embodiment of the disclosed technology.
Figure 12:
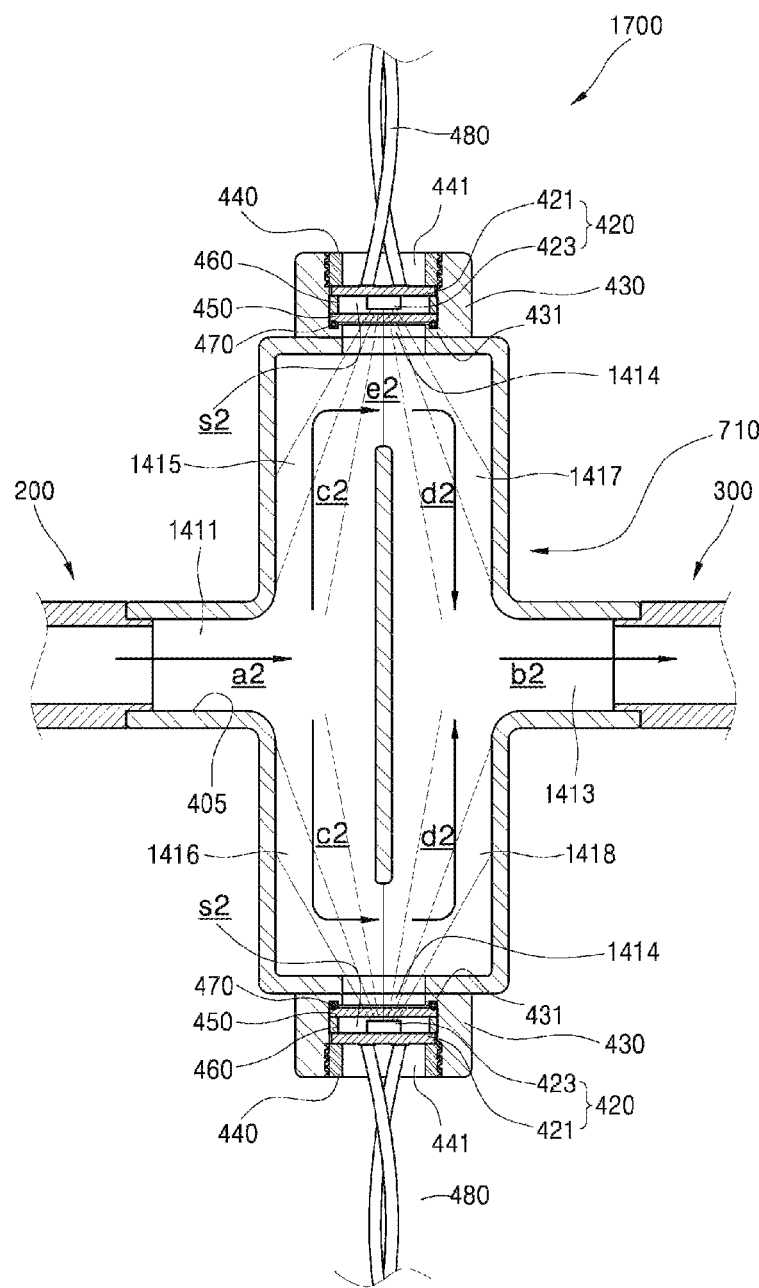
FIG. 12 is a cross-sectional view of the sterilization module according to a further embodiment of the disclosed technology upon sterilization of water.
Figure 13:
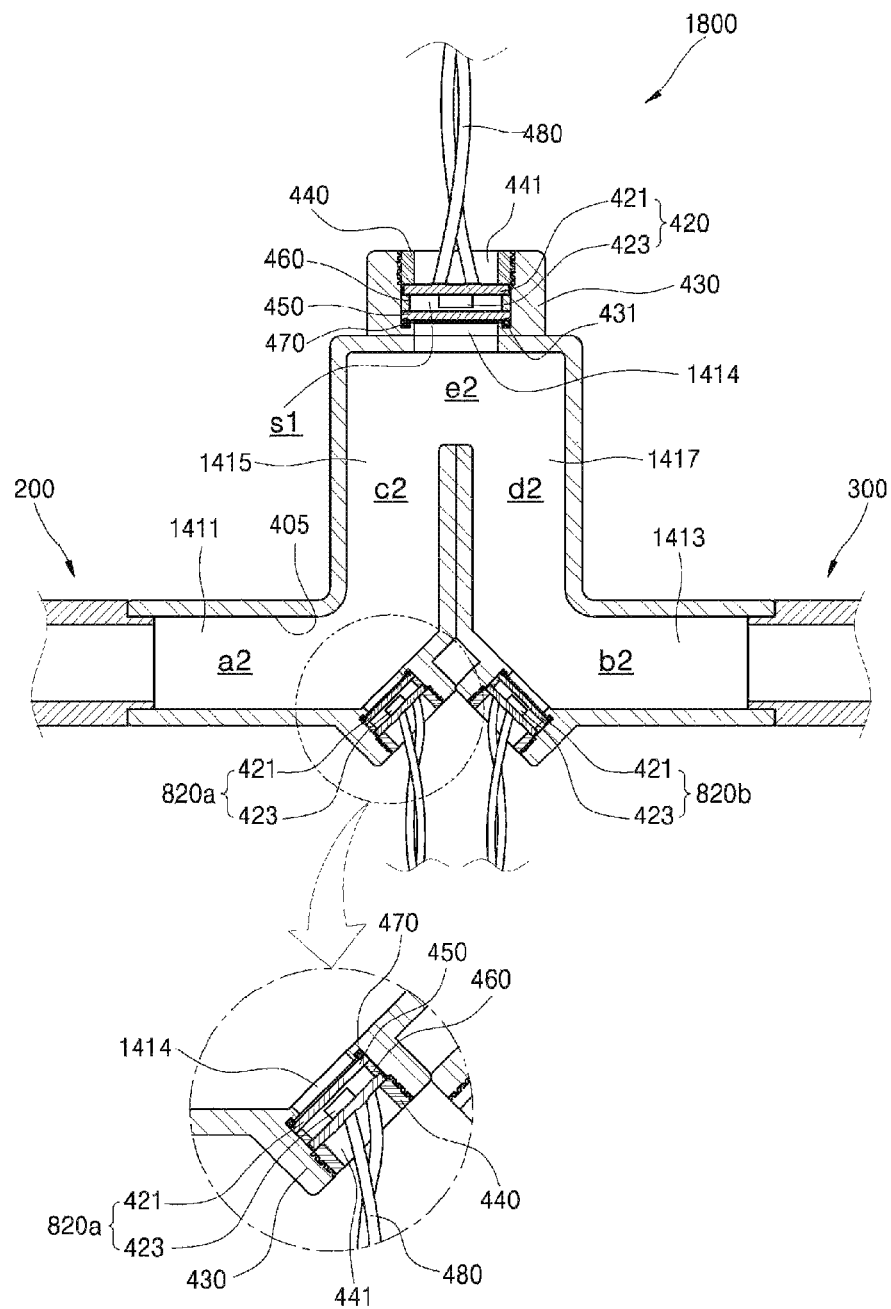
FIG. 13 is a cross-sectional view of a sterilization module according to yet another embodiment of the disclosed technology.
Figure 14:
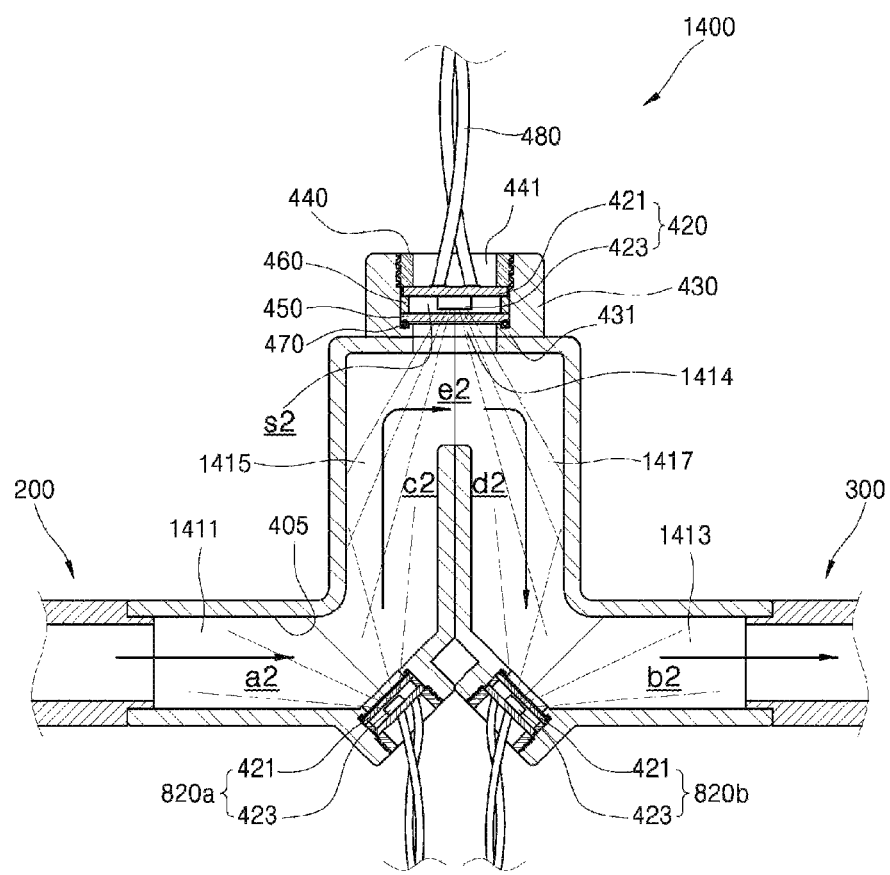
FIG. 14 is a cross-sectional view of the sterilization module according to yet another embodiment of the disclosed technology upon sterilization of water.

FIG. 11 is a cross-sectional view of a sterilization module according to a further embodiment of the disclosed technology and FIG. 12 is a cross-sectional view of the sterilization module according to this embodiment of the disclosed technology upon sterilization of water. Further, FIG. 13 is a cross-sectional view of a sterilization module according to yet another embodiment of the disclosed technology and FIG. 14 is a cross-sectional view of the sterilization module according to this embodiment of the disclosed technology upon sterilization of water.

Next, sterilization modules according to various embodiments of the disclosed technology and water purifiers including the same will be described with reference to FIG. 11 to FIG. 14.

For convenience of description, the same or similar components to those of the above embodiments are denoted by the same reference numerals and detailed descriptions thereof will be omitted.

Referring to FIG. 11 and FIG. 12, a sterilization module 1700 according to a further embodiment of the disclosed technology includes a flow channel body 710, a UV light emitting unit 420, a mounting unit 430, a holder 440, a protective cover 450, a spacer 460, a sealing member 470, and a cable 480.

The flow channel body 710 includes an inflow unit 1411, a discharge unit 1413, and a pair of bypass channel units 1415, 1416, 1417, 1418.

According to this embodiment, the pair of bypass channel units 1415, 1416, 1417, 1418 is disposed between the inflow unit 1411 and the discharge unit 1413 to be symmetrical with respect to an imaginary straight-line connecting the inflow channel a2 to the discharge channel b2.

In addition, an assembly of the UV light emitting unit 420, the mounting unit 430, the holder 440, the protective cover 450, the spacer 460, the sealing member 470 and the cable 480 (hereinafter referred to as a "UV light emitting unit assembly") is provided to each of the bypass channel units 1415, 1416, 1417, 1418.

That is, the sterilization module 1700 according to this embodiment has a structure wherein one bypass channel unit 1415, 1417 and the UV light emitting unit assembly provided to the bypass channel unit 1415, 1417 are disposed symmetrical to another bypass channel unit 1416, 1418 and another UV light emitting unit assembly provided to the bypass channel unit 1416, 1418 with reference to an imaginary line connecting the inflow channel a2 to the discharge channel b2.

Accordingly, the flow channel body 710 is formed with flow channels a2, b2, c2, d2, e2 such that two bypass channels c2, d2, e2 are bifurcated from one inflow channel a2 and connected to one discharge channel b2.

With this structure of the flow channels a2, b2, c2, d2, e2, the total volume of the flow channels a2, b2, c2, d2, e2 is enlarged, thereby reducing the flow rate of water flowing in the flow channels a2, b2, c2, d2, e2 while increasing a contact time and a contact area between water and UV light in the flow channels a2, b2, c2, d2, e2.

In addition, the UV light emitting unit 420 of the UV light emitting unit assemblies provided to each of the bypass channel units 1415, 1416, 1417, 1418 may emit UV light having strong sterilization characteristics towards the bypass channel units 1415, 1416, 1417, 1418.

As a result, not only can the entirety of the bypass channels c2, d2, e2 be uniformly irradiated with UV light, but also the UV light can be emitted in the same direction as the bypass channels c2, e2.

The sterilization module 1700 according to this embodiment employs the bypass channels c2, d2, e2 provided in the bifurcated structure to increase a contact time and a contact area between water and UV light in the flow channels a2, b2, c2, d2, e2 while allowing UV light to be emitted in the same direction as the bypass channels c2, e2, thereby further improving the effect of sterilizing water with UV light.

Referring to FIG. 13 and FIG. 14, a sterilization module 1800 according to yet another embodiment includes at least one of an inflow side UV light emitting unit 820a and a discharge side UV light emitting unit 820b. According to this embodiment, the sterilization module 1800 will be illustrated as including both the inflow side UV light emitting unit 820a and the discharge side UV light emitting unit 820b.

The inflow side UV light emitting unit 820a is disposed to emit UV light towards an inflow channel a2 and bypass channels c2, d2, e2, and the discharge side UV light emitting unit 820b is disposed to emit UV light towards the bypass channels c2, d2, e2 and a discharge channel b2.

Each of the inflow side UV light emitting unit 820a and the discharge side UV light emitting unit 820b includes a substrate 421 and a UV light emitting device 423.

The UV light emitting device 423 provided to the inflow side UV light emitting unit 820a is disposed on an imaginary bisector bisecting an internal angle defined between the inflow channel a2 and the bypass channels c2, d2, e2, specifically an internal angle defined by the inflow channel a2 in the interior region of the first bypass channel unit 1415.

For example, when the UV light emitting device 423 emits UV light at an emission angle of 120°, the inflow unit 1411 is connected to the first bypass channel unit 1415 such that the internal angle defined between the inflow channel a2 and the bypass channel c2 becomes 120° or less, preferably 90°, and the UV light emitting device 423 is disposed on an imaginary bisector bisecting an internal angle defined between the inflow channel a2 and the bypass channel c2 to emit UV light in an extension direction of the imaginary bisector.

In addition, the UV light emitting device 423 provided to the discharge side UV light emitting unit 820b is disposed on an imaginary bisector bisecting an internal angle defined by the bypass channels c2, d2, e2, more specifically an internal angle defined by the bypass channel e2 in the interior region of the second bypass channel 1417.

For example, when the UV light emitting device 423 emits UV light at an emission angle of 120°, the second bypass channel unit 1417 is connected to the discharge unit 1413 such that an internal angle defined between the bypass channel e2 and the discharge channel b2 becomes 120° or less, preferably 90°, and the UV light emitting device 423 is disposed on an imaginary bisector bisecting an internal angle defined between the bypass channel e2 and the discharge channel b2 to emit UV light in an extension direction of the imaginary bisector.

According to this embodiment, the sterilization module 1800 including the inflow side UV light emitting unit 820a and the discharge side UV light emitting unit 820b allows not only the bypass channels c2, d2, e2 but also the inflow channel a2 and the discharge channel b2 to be irradiated with UV light so as to increase a contact time and a contact area between water and UV light in the flow channels a2, b2, c2, d2, e2, while allowing UV light to be emitted in the same direction not only as the bypass channels c2, d2, e2 but also as the inflow channel a2 and the discharge channel b2, thereby further improving the effect of sterilizing water with UV light.

FIG. 15 to FIG. 19 show a sterilization module according to yet another embodiment of the disclosed technology.

Figure 15:
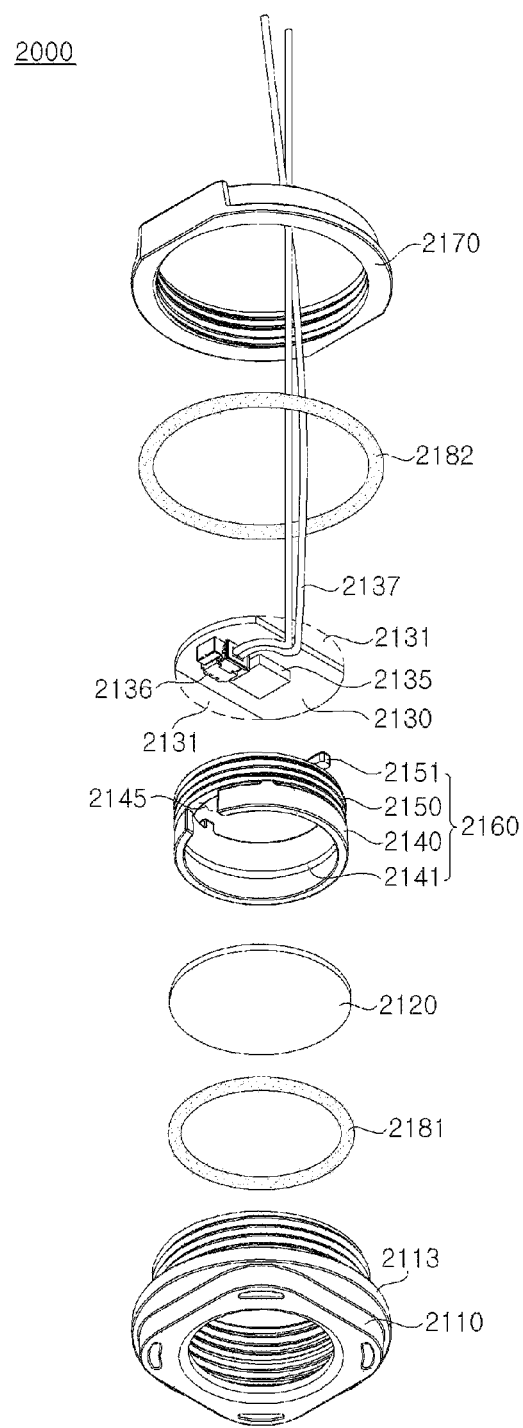
FIG. 15 is an exploded perspective view of a sterilization module according to yet another embodiment of the disclosed technology.
Figure 16:
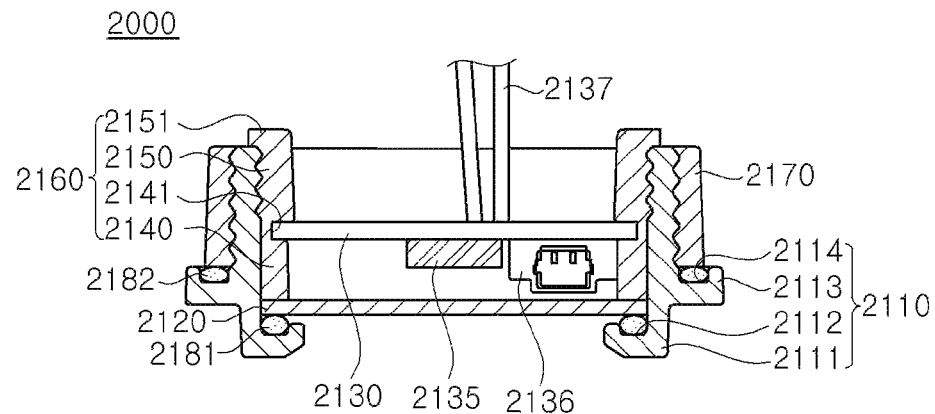
FIG. 16 is a side sectional view of the sterilization module according to yet another embodiment of the disclosed technology in an assembled state.
Figure 17:
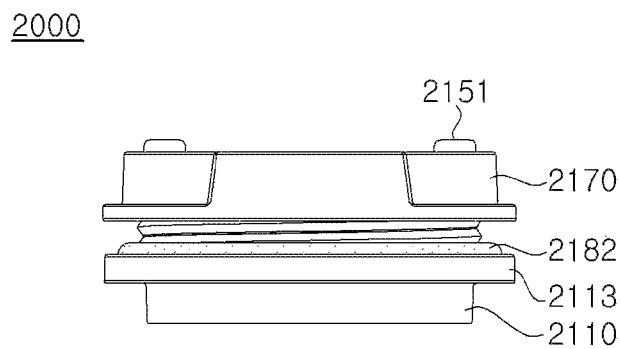
FIG. 17 is a front view of the sterilization module according to yet another embodiment of the disclosed technology in an assembled state.
Figure 18:
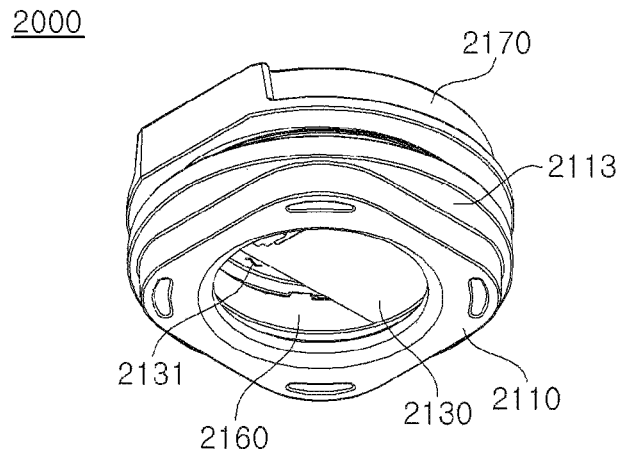
FIG. 18 is a bottom perspective view of the sterilization module according to yet another embodiment of the disclosed technology in an assembled state.
Figure 19:
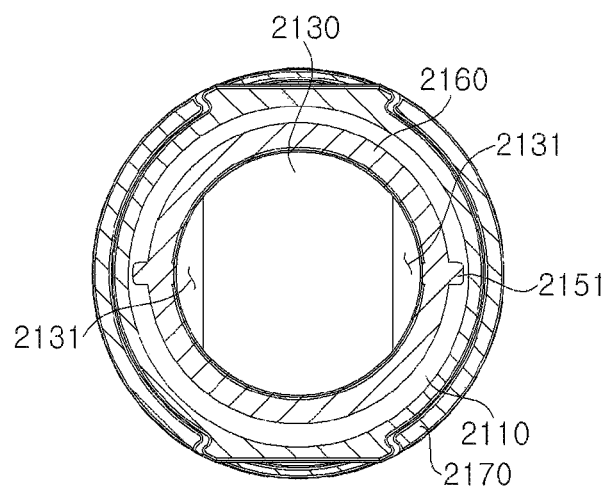
FIG. 19 is a bottom view of the sterilization module according to yet another embodiment of the disclosed technology in an assembled state.

FIG. 15 is an exploded perspective view of a sterilization module according to yet another embodiment of the disclosed technology. FIG. 16 is a side sectional view of the sterilization module according to this embodiment of the disclosed technology in an assembled state. In addition, FIG. 17 is a front view of the sterilization module according to this embodiment of the disclosed technology in an assembled state. Further, FIG. 18 is a bottom perspective view of the sterilization module according to this embodiment of the disclosed technology in an assembled state. Further, FIG. 19 is a bottom view of the sterilization module according to this embodiment of the disclosed technology in an assembled state.

Referring to FIG. 15 to FIG. 19, a sterilization module 2000 includes a main body 2110, a protective cover 2120, a substrate 2130, a UV light emitting device 2135, a connector 2136, a cable 2137, an inner holder 2160, and an outer holder 2170.

According to this embodiment, the main body 2110 is open at upper and lower sides thereof. That is, the main body 2110 has a hollow internal space open at upper and lower sides thereof. In the internal space of the main body 2110, the protective cover 2120, the substrate 2130, the UV light emitting device 2135, the connector 2136, and the inner holder 2160 are disposed.

According to this embodiment, the main body 2110 is formed at a lower side thereof with a seat portion 2111. The seat portion 2111 protrudes inward from an inner surface of the main body 2110.

According to this embodiment, the UV light emitting device 2135 is disposed above the seat portion 2111. Accordingly, UV light emitted from the UV light emitting device 2135 is discharged through the seat portion 2111. Since UV light is emitted in a radial direction, the UV light can be reflected by an inner wall of the seat portion 2111. Thus, according to this embodiment, a portion of an inner surface of the seat portion 2111 has a tapered structure having a diameter gradually increasing towards a lower surface thereof. Here, the lower surface of the seat portion 2111 corresponds to a lower surface of the main body 2110. With the structure wherein the inner surface of the seat portion 2111 has the tapered structure, the intensity of UV light reflected by the seat portion 2111 is decreased and the intensity of UV light discharged to the outside without being reflected is increased. As such, the seat portion 2111 having the tapered structure improves the effect of emitting UV light, thereby improving the sterilization effects of the sterilization module 2000.

According to this embodiment, the seat portion 2111 is formed on an upper surface thereof with an inner sealing member groove 2112. An inner sealing member 2181 is inserted into the inner sealing member groove 2112. The inner sealing member 2181 inserted into the inner sealing member groove 2112 is disposed between the upper surface of the seat portion 2111 and a lower surface of the protective cover 2120. With this arrangement, the inner sealing member 2181 seals a gap between the main body 2110 and the protective cover 2120. The inner sealing member 2181 stably shields the interior of the main body 2110 from the outside, thereby improving a waterproofing function of the sterilization module 2000. According to this embodiment, the inner sealing member 2181 may be formed of an elastic material. For example, the inner sealing member 2181 may be a rubber sealing member, such as an O-ring.

According to this embodiment, the main body 2110 is formed with a body holding portion 2113. The body holding portion 2113 is formed along an outer peripheral surface of the main body 2110. In addition, the body holding portion 2113 protrudes from the outer surface of the main body 2110. With this structure, the body holding portion 2113 serves to secure the sterilization module 2000 such that a lower portion of the sterilization module 2000 is placed inside the water reservoir (not shown) when the sterilization module 2000 is mounted on the water reservoir (not shown).

According to this embodiment, the body holding portion 2113 is formed on an upper surface thereof with an outer sealing member groove 2114. The outer sealing member 2182 is inserted into the outer sealing member groove 2114. The outer sealing member 2182 inserted into the outer sealing member groove 2114 is disposed between the upper surface of the body holding portion 2113 and a lower surface of the outer holder 2170. With this arrangement, the outer sealing member 2182 stably shields the interior of the sterilization module 2000 from the outside, thereby improving the waterproofing function of the sterilization module 2000. According to this embodiment, the outer sealing member 2182 may be formed of an elastic material. For example, the outer sealing member 2182 may be a rubber sealing member, such as an O-ring.

According to this embodiment, the protective cover 2120 is seated on the upper surface of the seat portion 2111 of the main body 2110. The protective cover 2120 seated on the seat portion 2111 shields the interior of the main body 2110 from the outside. The protective cover 2120 allows UV light emitted from the UV light emitting device 2135 to pass therethrough. That is, the protective cover 2120 is formed of a UV transmissive material. For example, the protective cover 2120 may include at least one of quartz, a poly(methyl methacrylate) resin, and a fluorine-based polymer resin.

According to this embodiment, UV light emitted from the UV light emitting device 2135 can be spread or scattered while passing through the protective cover 2120.

According to this embodiment, the substrate 2130 is secured inside the main body 2110 by the inner holder 2160. For example, the substrate 2130 may be a printed circuit board (PCB), a metal substrate, a ceramic substrate, or the like. That is, the substrate 2130 may be selected from any kind of substrate capable of being electrically connected to the UV light emitting device 2135.

According to this embodiment, the main body 2110 has a connection path 2131 which connects an upper space on the substrate 2130 to a lower space under the substrate 2130.

According to this embodiment, the connection path 2131 is formed to penetrate the substrate 2130. Referring to FIG. 15, the connection path 2131 is a space formed by dividing both sides of the substrate 2130 and defined between an inner wall of the inner holder 2160 and the substrate 2130. Although the connection path 2131 according to this embodiment is shown in FIG. 15, it should be understood that the connection path 2131 according to the disclosed technology is not limited thereto. The connection path 2131 may have any structure allowing the cable 2137 to pass therethrough. For example, the connection path 2131 may be formed in a hole shape which penetrates the substrate 2130.

According to this embodiment, with the structure of the connection path 2131 in the substrate 2130, a contact area between the substrate 2130 and air can be increased. Further, the connection path 2131 enables air circulation between the upper space on the substrate 2130 and the lower space under the substrate 2130 or the outside. Thus, heat generated from the substrate 2130, the connector 2136 and the UV light emitting device 2135 can be easily transferred to the outside through the connection path 2131, thereby improving heat dissipation of the sterilization module 2000.

According to this embodiment, the UV light emitting device 2135 is mounted on the lower surface of the substrate 2130. The UV light emitting device 2135 is electrically connected to the substrate 2130. The UV light emitting device 2135 emits UV light towards the protective cover 2120. UV light emitted from the UV light emitting device 2135 has a sterilization effect. For example, the UV light emitting device 2135 emits UV light in the wavelength range of 200 nm to 280 nm, corresponding to the UVC region. The wavelength range of ultraviolet light emitted from the UV light emitting device 2135 may vary depending upon target microorganisms. According to this embodiment, the UV light emitting device 2135 is a light emitting diode chip.

According to this embodiment, the connector 2136 is mounted on the lower surface of the substrate 2130. In addition, the connector 2136 is biased towards one side from the center of the substrate 2130 when mounted on the substrate 2130.

Further, the connector 2136 is electrically connected to the substrate 2130. The connector 2136 delivers external power to the substrate 2130 via the cable 2137. Referring to FIG. 15 and FIG. 16, the connector 2136 is shown as being mounted on the lower surface of the substrate 2130. However, it should be understood that the disclosed technology is not limited thereto. Alternatively, the connector 2136 may be mounted on the upper surface of the substrate 2130.

According to this embodiment, the cable 2137 is inserted into the connector 2136 to be electrically connected thereto. One end of the cable 2137 is inserted into the connector 2136 and the other end of the cable 2137 is placed outside after passing through the inner holder 2160. For example, the other end of the cable 2137 is connected to an external power supply (not shown). The cable 2137 transmits electric power supplied from the external power supply (not shown) to the connector 2136. Accordingly, power is supplied from of the external power supply (not shown) to the cable 2137, the connector 2136, the substrate 2130, and the UV light emitting device 2135, thereby operating these components. According to this embodiment, the cable 2137 is detachably coupled to the connector 2136.

When the connector 2136 is mounted on the lower surface of the substrate 2130 as shown in FIG. 15 to FIG. 19, the one end of the cable 2137 is inserted into the connector 2136 through the connection path 2131 of the substrate 2130.

According to this embodiment, the inner holder 2160 is disposed on the protective cover 2120. Further, a portion of the inner holder 2160 is fastened to the inner wall of the main body 2110. Accordingly, the inner holder 2160 is secured to the inner wall of the main body 2110.

According to this embodiment, an inner wall of the inner holder 2160 is formed with a substrate fitting groove 2141. The substrate 2130 is fitted into the substrate fitting groove 2141 and is secured inside the inner holder 2160. Here, the lower surface of the substrate 2130 faces the lower surface of the main body 2110 and the upper surface of the substrate 2130 faces the upper surface of the main body 2110.

According to this embodiment, the inner holder 2160 can be divided into a spacer 2140 and a fixing holder 2150. It is noted that this division is provided for convenience of description and the inner holder 2160 according to this embodiment is an integral body in which the spacer 2140 is integrally connected to the fixing holder 2150. The substrate fitting groove 2141 is formed in the spacer 2140. That is, a lower portion of the inner holder 2160 constitutes the spacer 2140 and an upper portion of the inner holder 2160 constitutes the fixing holder 2150.

According to this embodiment, the spacer 2140 is disposed between the substrate 2130 and the protective cover 2120. The spacer 2140 separates the UV light emitting device 2135 from the protective cover 2120. That is, the spacer 2140 forms a separation space between the UV light emitting device 2135 and the protective cover 2120. The separation space allows UV light radially emitted from the UV light emitting device 2135 to be incident on the overall surface of the protective cover 2120.

According to this embodiment, the spacer 2140 is formed with a side opening 2145. The side opening 2145 is formed in a structure wherein the spacer 2140 is partially open at one side thereof. The side opening 2145 receives the connector 2136 mounted on the lower surface of the substrate 2130. That is, the spacer 2140 is open at one side thereof corresponding to one side of the substrate towards which the connector 2136 is biased.

The spacer 2140 having the side opening 2145 allows the substrate 2130 having the connector 2136 mounted thereon to be easily inserted into the inner holder 2160. For example, with the substrate 2130 inserted into the inner holder 2160 through the side opening 2145, the side surface of the substrate 2130 can be fitted into the substrate fitting groove 2141.

According to this embodiment, the fixing holder 2150 corresponds to a region of the inner holder 2160 disposed on the substrate 2130. The fixing holder 2150 is fastened to the inner wall of the main body 2110. For example, an outer wall of the fixing holder 2150 is fastened to the inner wall of the main body 2110 by screw coupling. As the outer wall of the fixing holder 2150 is fastened to the inner wall of the main body 2110, the inner holder 2160 is secured inside the main body 2110.

According to this embodiment, the inner holder 2160 is formed at the upper portion thereof with a depth adjusting portion 2151. As shown in FIG. 15 to FIG. 19, the depth adjusting portion 2151 protrudes from an upper surface of the fixing holder 2150 towards the outside of the fixing holder 2150. Although not shown in the drawings, the depth adjusting portion 2151 may protrude outward from an outer surface of the fixing holder 2150.

According to this embodiment, the depth adjusting portion 2151 prevents the inner holder 2160 from being inserted into the main body 2110 by a predetermined depth or more when the inner holder 2160 is coupled to the main body 2110. Thus, the depth adjusting portion 2151 can prevent damage to the protective cover 2120 by preventing the inner holder 2160 from being excessively deeply inserted into the main body 2110. In addition, the depth adjusting portion 2151 is formed to protrude outward from the main body 2110 or the outer holder 2170 when the inner holder 2160 is coupled to the main body 2110. With this structure, the depth adjusting portion 2151 acts as a handle. That is, when a user wants to detach the inner holder 2160 from the main body 2110, the user can easily detach the inner holder 2160 therefrom by gripping the depth adjusting portion 2151, which protrudes outward from the main body 2110, without a separate device.

According to this embodiment, the outer holder 2170 is fastened to an outer wall of the main body 2110. For example, an inner wall of the outer holder 2170 is fastened to the outer wall of the main body 2110 by screw coupling. Accordingly, a portion of the main body 2110 is secured inside the outer holder 2170.

The sterilization module 2000 according to this embodiment allows detachable assembly of the main body 2110 to the inner holder 2160. Accordingly, the sterilization module 2000 according to this embodiment enables replacement of malfunctioning components with new ones after detaching the inner holder 2160 when there is a malfunction of components of the sterilization module, such as the substrate 2130, the UV light emitting device 2135, the connector 2136, and the like.

Figure 20:
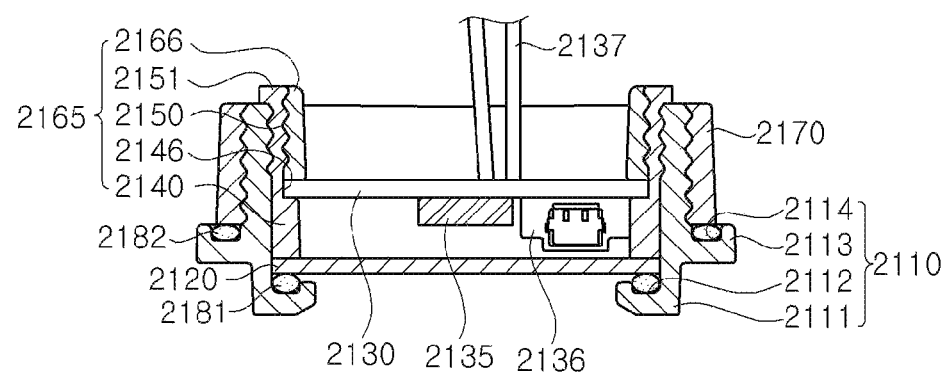
FIG. 20 is a side sectional view of a sterilization module according to yet another embodiment of the disclosed technology.

FIG. 20 is a side sectional view of a sterilization module according to yet another embodiment of the disclosed technology.

In the following description of a sterilization module 2100 according to yet another embodiment, repeated description of the same or similar components to the sterilization module shown in FIG. 15 to FIG. 19 will be omitted. For description of the same or similar components, reference can be made to FIG. 15 to FIG. 19.

Referring to FIG. 20, an inner holder 2165 of the sterilization module 2100 includes a substrate seat 2146 and a substrate holding portion 2166.

In some implementations, the substrate seat 2146 may be integrally formed with the spacer 2140 as shown in FIG. 20. In this case, the substrate seat 2146 may be located on the spacer 2140 to receive the substrate 2130. For example, the substrate seat 2146 may have a shape having a vertical part and a horizontal part protruding from the vertical part. For example, the substrate seat 2146 may have a "∟" shape. A substrate 2130 is seated on a surface or the horizontal part of the substrate seat 2146. In some implementations, the substrate seat 2146 can be implemented as a separate element from the spacer 2140. In some implementations, the substrate seat 2146, the spacer 2140, and the fixing holder 2150 may be integrally formed. In this case, the substrate seat 2146 has a protruding portion toward the UV light emitting device 2135 with reference to a sidewall of the spacer and/or the fixing holder 2150. In some implementations, the substrate seat 2146, the spacer 2140, and the fixing holder may be formed separately from one another.

According to this embodiment, with the substrate seat 2146, the inner holder 2165 is composed of the spacer 2140 and the fixing holder 2150 having a larger inner diameter than the spacer 2140. Since the inner diameter of the fixing holder 2150 is larger than that of the spacer 2140, the substrate 2130 can be easily disposed inside the inner holder 2165.

According to this embodiment, the substrate holding portion 2166 is disposed on the substrate 2130 to be fastened to the inner wall of the fixing holder 2150. For example, the substrate holding portion 2166 may be fastened to the fixing holder 2150 through screw coupling. Upon fastening of the substrate holding portion 2166 to the fixing holder 2150, the substrate holding portion 2166 may compress the substrate 2130. Accordingly, the substrate 2130 is disposed between the substrate seat 2146 and the substrate holding portion 2166. Further, with the substrate 2130 seated on the substrate seat 2146, the substrate holding portion 2166 is fastened to the fixing holder 2150, so that the substrate 2130 is secured inside the inner holder 2165.

Figure 21:
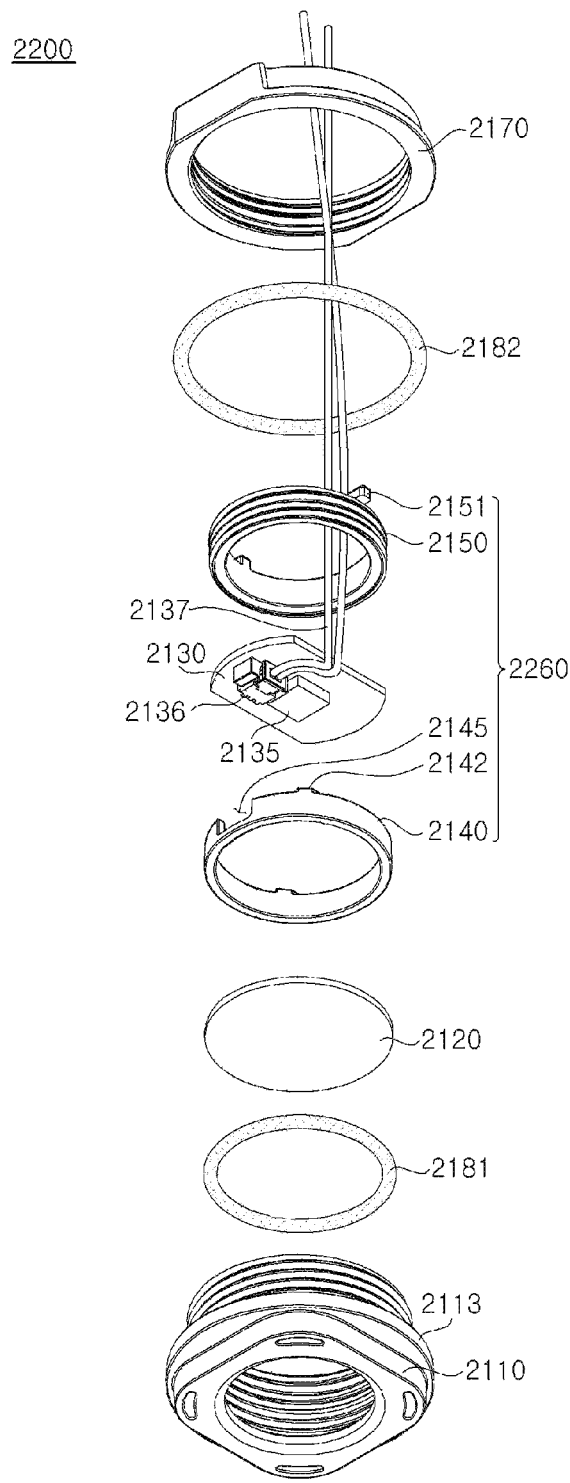
FIG. 21 is an exploded perspective view of a sterilization module according to yet another embodiment of the disclosed technology.
Figure 22:
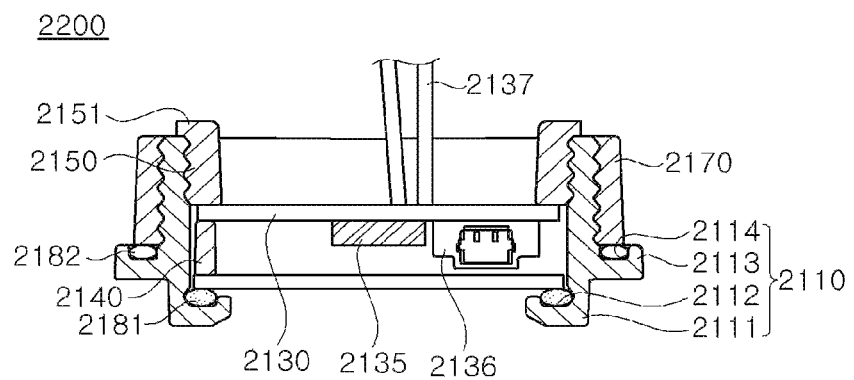
FIG. 22 is a side sectional view of the sterilization module according to yet another embodiment of the disclosed technology in an assembled state.

FIG. 21 and FIG. 22 illustrate a sterilization module according to yet another embodiment of the disclosed technology.

FIG. 21 is an exploded perspective view of the sterilization module according to yet another embodiment of the disclosed technology. FIG. 22 is a side sectional view of the sterilization module according to yet another embodiment of the disclosed technology in an assembled state.

In the following description of a sterilization module 2200 according to yet another embodiment, repeated description of the same or similar components to the sterilization module shown in FIG. 15 to FIG. 19 will be omitted. For description of the same or similar components, reference can be made to FIG. 15 to FIG. 19.

Referring to FIG. 21 and FIG. 22, the sterilization module 2200 includes a main body 2110, a protective cover 2120, a substrate 2130, a UV light emitting device 2135, a connector 2136, a cable 2137, an inner holder 2260, and an outer holder 2170. The protective cover 2120, the inner holder 2260, the substrate 2130 and the UV light emitting device 2135 are disposed in the main body 2110. Further, an upper portion of the main body 2110 is inserted into the outer holder 2170 to be secured thereto.

According to this embodiment, the inner holder 2260 can be divided into a spacer 2140 and a fixing holder 2150. In this embodiment, the spacer 2140 and the fixing holder 2150 are separate components separated from each other.

According to this embodiment, the spacer 2140 is formed with a side opening 2145 and a displacement preventing portion 2142. For the structure and description of the side opening 2145, reference can be made to FIG. 15 to FIG. 19. The displacement preventing portion 2142 protrudes upwards from an upper surface of the spacer 2140. The displacement preventing portion 2142 prevents the substrate 2130 mounted on the upper surface of the spacer 2140 from being displaced from a designated place. For example, when the substrate 2130 is seated on the spacer 2140, the substrate 2130 is placed only inside the displacement preventing portion 2142 by the displacement preventing portion 2142. The height of the displacement preventing portion 2142 is less than or equal to the thickness of the substrate 2130. Thus, when the fixing holder 2150 is fastened to the main body 2110, the fixing holder 2150 can directly compress the substrate 2130.

According to this embodiment, the fixing holder 2150 is disposed on the substrate 2130 seated on the spacer 2140. In addition, the fixing holder 2150 is fastened to the inner wall of the main body 2110. For example, the outer wall of the fixing holder 2150 is fastened to the inner wall of the main body 2110 through screw coupling.

According to this embodiment, the substrate 2130 is disposed between the spacer 2140 and the fixing holder 2150. Thus, when the fixing holder 2150 is fastened to the inner wall of the main body 2110, the fixing holder 2150 compresses the substrate 2130 in a downward direction. Here, the substrate 2130 is more stably secured inside the main body 2110 by the spacer 2140, which is disposed under the substrate 2130 and supports the substrate 2130, and the fixing holder 2150, which is disposed on the substrate 2130 and compresses the substrate 2130.

Figure 23:
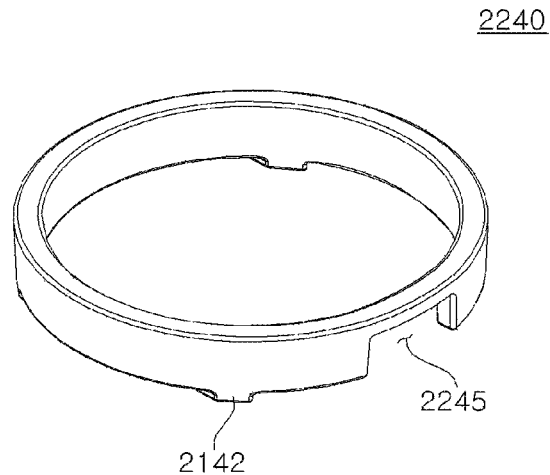
FIG. 23 and FIG. 24 are perspective views of a spacer according to embodiments of the disclosed technology.
Figure 24:
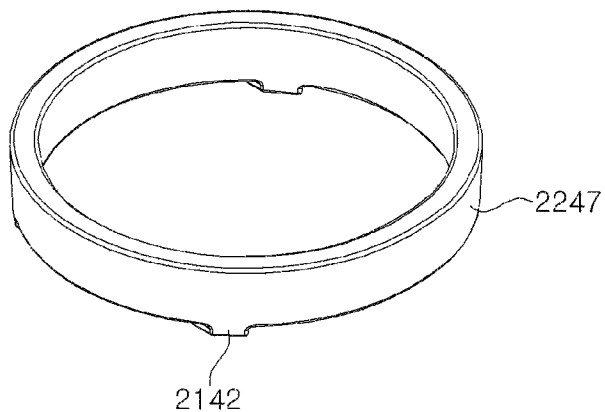

FIG. 23 and FIG. 24 illustrate spacers according to other embodiments of the disclosed technology.

A spacer 2240 according to another embodiment of the invention has the same function as the spacer shown in FIG. 21 and FIG. 22. A repeated description of the same components of the spacer 2240 as those of the spacer shown in FIG. 21 and FIG. 22 will be omitted. For description of the same components, reference can be made to FIG. 21 and FIG. 22.

Referring to FIG. 23, the spacer 2240 is formed with a side-opening groove 2245 and a displacement preventing portion 2142. For description of the displacement preventing portion 2142, reference can be made to FIG. 21 and FIG. 22.

According to this embodiment, the spacer 2240 is open at one side thereof corresponding to a place at which a side connector 136 (see FIG. 21 and FIG. 22) is disposed. Specifically, the side-opening groove 2245 is formed in a groove structure, which is formed on a lower surface of the spacer 2240 to have a partially open side surface. With this structure, the side-opening groove 2245 receives the connector 2136 mounted on the lower surface of the substrate 2130.

Referring to FIG. 24, the spacer 2247 is formed with a displacement preventing portion 2142. For description of the displacement preventing portion 2142, reference can be made to FIG. 21 and FIG. 22.

In this embodiment, the spacer 2247 has a cylindrical structure. The side opening 145 (see FIG. 21) or the side-opening groove 245 (see FIG. 23) can be omitted depending on the location of the connector 135 (see FIG. 21 and FIG. 22). For example, in a structure wherein the connector 136

(see FIG. 22) is disposed on the upper surface of the substrate 130 (see FIG. 22), the side opening 145 (see FIG. 21) or the side-opening groove 245 (see FIG. 23) can be omitted. In addition, in a structure wherein the connector 136 (see FIG. 22) has a small size, the side opening 145 (see FIG. 21) or the side-opening groove 245 (see FIG. 23) can also be omitted.

In the structure wherein the spacer 2247 does not include the side opening 145 (see FIG. 21) or the side-opening groove 245 (see FIG. 23), the spacer 2247 can be fabricated through a simple process with reduced costs and time.

Figure 25:
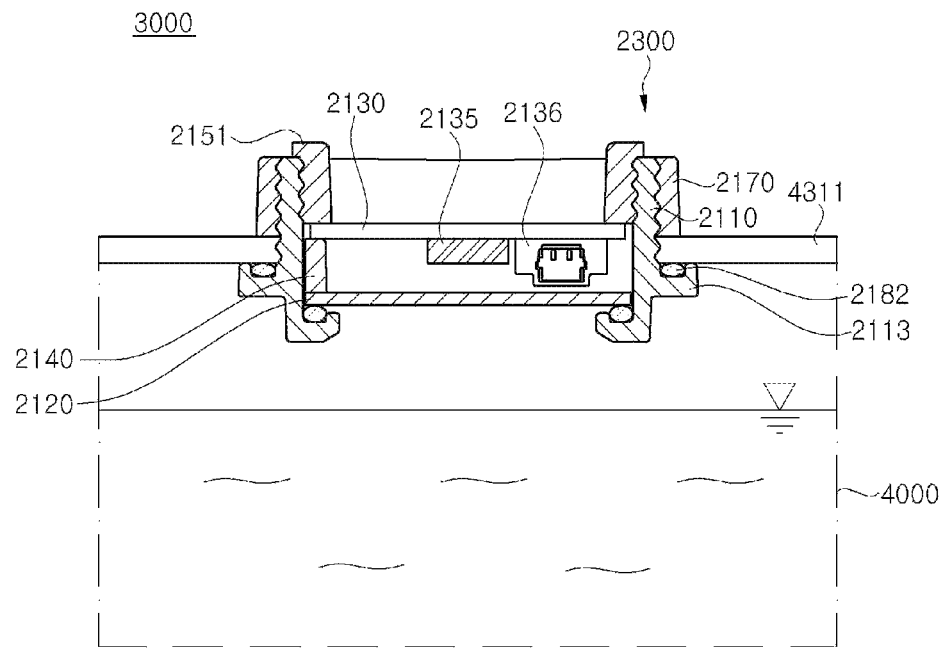
FIG. 25 is a side sectional view of a water purifier according to a further embodiment of the disclosed technology.

FIG. 25 is a side sectional view of a water purifier according to a further embodiment of the disclosed technology.

Referring to FIG. 25, a water purifier 3000 according to this embodiment includes a water reservoir 4000 and a sterilization module 2300.

According to this embodiment, the water purifier 3000 according to this embodiment purifies water by sterilizing water stored in the water reservoir 4000 using the sterilization module 2300.

According to this embodiment, water is stored in the water reservoir 4000. Although not shown in FIG. 25, the water reservoir 4000 is formed with an inlet port through which water is supplied to the water reservoir and a discharge port through which water is discharged from the water reservoir.

According to this embodiment, the sterilization module 2300 is provided to the water reservoir 4000 through one surface of the water reservoir 4000. The sterilization module 2300 is one of the sterilization modules shown in FIG. 15 to FIG. 24. For a detailed description of the components of the sterilization module 2300, reference can be made to FIG. 15 to FIG. 24.

Referring to FIG. 25, the sterilization module 2300 is provided to the water reservoir 4000 through an upper surface of the water reservoir 4000. A lower portion of the sterilization module 2300 is placed inside the water reservoir 4000 and an upper portion of the sterilization module 2300 is placed outside the water reservoir 4000. Specifically, the body holding portion 2113 and a portion of the main body 2110 disposed under the body holding portion 2113 are placed inside the water reservoir 4000. In addition, a portion of the main body 2110 on the body holding portion 2113 and the outer holder 2170 are placed outside the water reservoir 4000. Accordingly, an inner wall of the water reservoir 4000 contacts the upper surface of the body holding portion 2113. In addition, an outer wall of the water reservoir 4000 contacts a lower surface of the outer holder 2170.

Here, a waterproofing effect of the sterilization module 2300 is improved by the outer sealing member 2182 disposed between the upper surface of the body holding portion 2113 and the inner wall of the water reservoir 4000.

According to this embodiment, the sterilization module 2300 emits UV light towards the surface of water stored in the water reservoir 4000. The water stored in the water reservoir 4000 is purified through sterilization by UV light emitted from the sterilization module 2300.

In the water purifier 3000 according to the embodiment shown in FIG. 25, the sterilization module 2300 is mounted on the upper surface of the water reservoir 4000. However, it should be understood that the disclosed technology is not limited thereto. Alternatively, the water purifier 3000 may have a structure wherein the sterilization module 2300 is mounted on a side or lower surface of the water reservoir 4000. For example, in the structure wherein the sterilization module 2300 is mounted on the side surface of the water reservoir 4000, the sterilization module 2300 emits UV light towards the surface of the water or into the water stored in the water reservoir 4000. Further, in the structure wherein the sterilization module 2300 is mounted on the lower surface of the water reservoir 4000, the sterilization module 2300 emits UV light into the water stored in the water reservoir 4000.

The main body 2110 is fitted into the water reservoir 4000 from inside to outside such that an upper portion of the main body 2110 is exposed outside the water reservoir 4000 therethrough. Here, the lower portion of the main body 2110 is disposed inside the water reservoir 4000 by the body holding portion 2113 of the main body 2110. Then, the outer holder 2170 is fastened to the outer wall of the main body 2110 outside the water reservoir 4000. Here, as the outer holder 2170 is fastened to the main body 2110, the outer holder 2170 compresses the outer wall of the water reservoir 4000. Thus, the sterilization module 2300 is secured to the water reservoir 4000 by the body holding portion 2113 and the outer holder 2170 of the main body 2110. In addition, the water stored in the water reservoir 4000 can be prevented from flowing into the sterilization module 2300 by the outer sealing member 2182 inserted into the main body 2110.

FIG. 26 to FIG. 29 illustrate the structure wherein the sterilization module is mounted on the water purifier according to the embodiment of the disclosed technology.

According to this embodiment, one surface 4311 of the water reservoir is detachably attached to a body of the water reservoir. For example, if the one surface 4311 of the water reservoir is an upper surface of the water reservoir, the body of the water reservoir is composed of a lower surface and a side surface. Thus, with the sterilization module 2300 mounted on the one surface 4311 of the water reservoir, the one surface 4311 may be assembled to the body of the water reservoir. In this way, the sterilization module 2300 can be provided to the water reservoir in the structure wherein the sterilization module 2300 penetrates the water reservoir.

Figure 26:
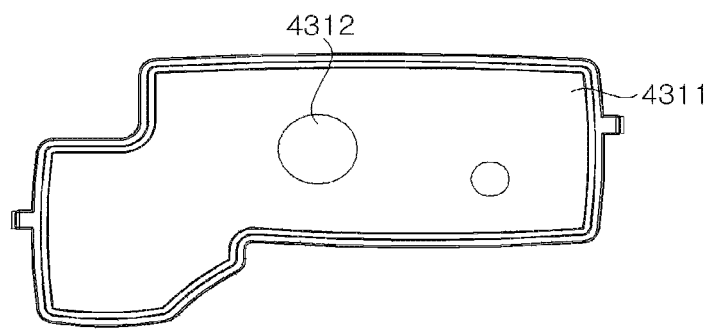
FIG. 26 is a top view illustrating an upper side of one surface of the water reservoir on which the sterilization module according to the embodiments of the disclosed technology is mounted.

FIG. 26 is a top view illustrating an upper side of one surface of the water reservoir on which the sterilization module according to the embodiments of the disclosed technology is mounted.

Referring to FIG. 26, the one surface 4311 of the water reservoir is formed with a sterilization module mounting hole 4312 in which the sterilization module 2300 is mounted. A diameter of the sterilization module mounting hole 4312 is larger than or equal to an outer diameter of the upper portion of the main body 2110. In addition, the diameter of the sterilization module mounting hole 4312 is smaller than outer diameters of the body holding portion 2113 and the outer holder 2170 of the main body 2110.

Figure 27:
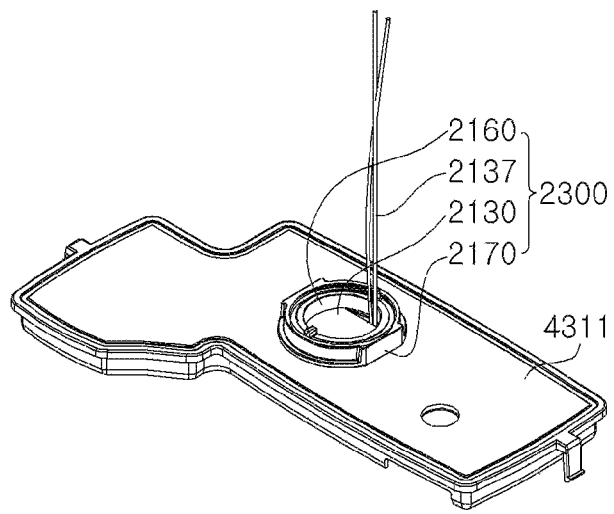
FIG. 27 is a perspective view illustrating the one surface of the water reservoir on which the sterilization module according to the embodiments of the disclosed technology is mounted.

FIG. 27 is a perspective view illustrating the one surface of the water reservoir on which the sterilization module according to the embodiments of the disclosed technology is mounted.

Referring to FIG. 27, the sterilization module 2300 is inserted into the sterilization module mounting hole 4312 formed in the one surface 4311 of the water reservoir. Here, the upper portion of the main body 2110 is inserted into the sterilization module mounting hole 4312 in an upward direction from a lower side of the one surface 4311 of the water reservoir. Due to the size of the sterilization module mounting hole 4312, the lower portion of the sterilization module 2300 is placed under the one surface 4311 of the water reservoir and the upper portion of the sterilization module 2300 is placed on the one surface 4311 of the water reservoir. Thereafter, the upper portion of the main body 2110 is coupled to the outer holder 2170 on the one surface 4311 of the water reservoir, so that the sterilization module 2300 is mounted on the one surface 4311 of the water reservoir.

According to this embodiment, after mounting all components of the sterilization unit inside the main body 2110 excluding the outer holder 2170, the main body 2110 may be mounted on the one surface 4311 of the water reservoir. Alternatively, with the main body 2110 mounted on the one surface 4311 of the water reservoir, the remaining components of the sterilization module 2300 may be disposed outside and inside the main body 2110.

Figure 28:
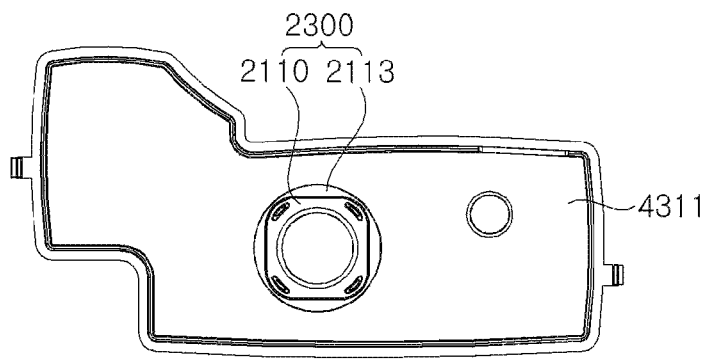
FIG. 28 is a bottom view illustrating a lower side of the one surface of the water reservoir on which the sterilization module according to the embodiments of the disclosed technology is mounted.

FIG. 28 is a bottom view illustrating a lower side of the one surface of the water reservoir on which the sterilization module according to the embodiments of the disclosed technology is mounted.

Referring to FIG. 28, a lower portion of the sterilization module 2300 is disposed on the lower side of the one surface 4311 of the water reservoir. Here, the lower portion of the sterilization module 2300 refers to the lower portion of the main body 2110 including the body holding portion 2113. According to this embodiment, the lower side of the one surface 4311 of the water reservoir faces the interior of the body of the water reservoir. Accordingly, the lower portion of the sterilization module 2300 is disposed inside the water reservoir.

Figure 29:
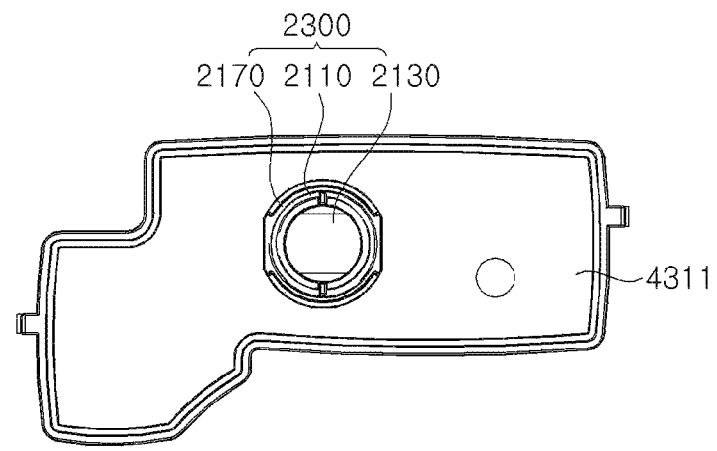
FIG. 29 is a top view illustrating the upper side of the one surface of the water reservoir on which the sterilization module according to the embodiments of the disclosed technology is mounted.

FIG. 29 is a top view illustrating the upper side of the one surface of the water reservoir on which the sterilization module according to the embodiments of the disclosed technology is mounted.

Referring to FIG. 29, an upper portion of the sterilization module 2300 is disposed on an upper side of the one surface 4311 of the water reservoir. Here, the upper portion of the sterilization module 2300 refers to the outer holder 2170 and a portion of the main body 2110 corresponding to an upper portion of the body holding portion 2113. According to this embodiment, the upper side of the one surface 4311 of the water reservoir faces outside the body of the water reservoir. Accordingly, the lower portion of the sterilization module 2300 is disposed outside the water reservoir.

Figure 30:
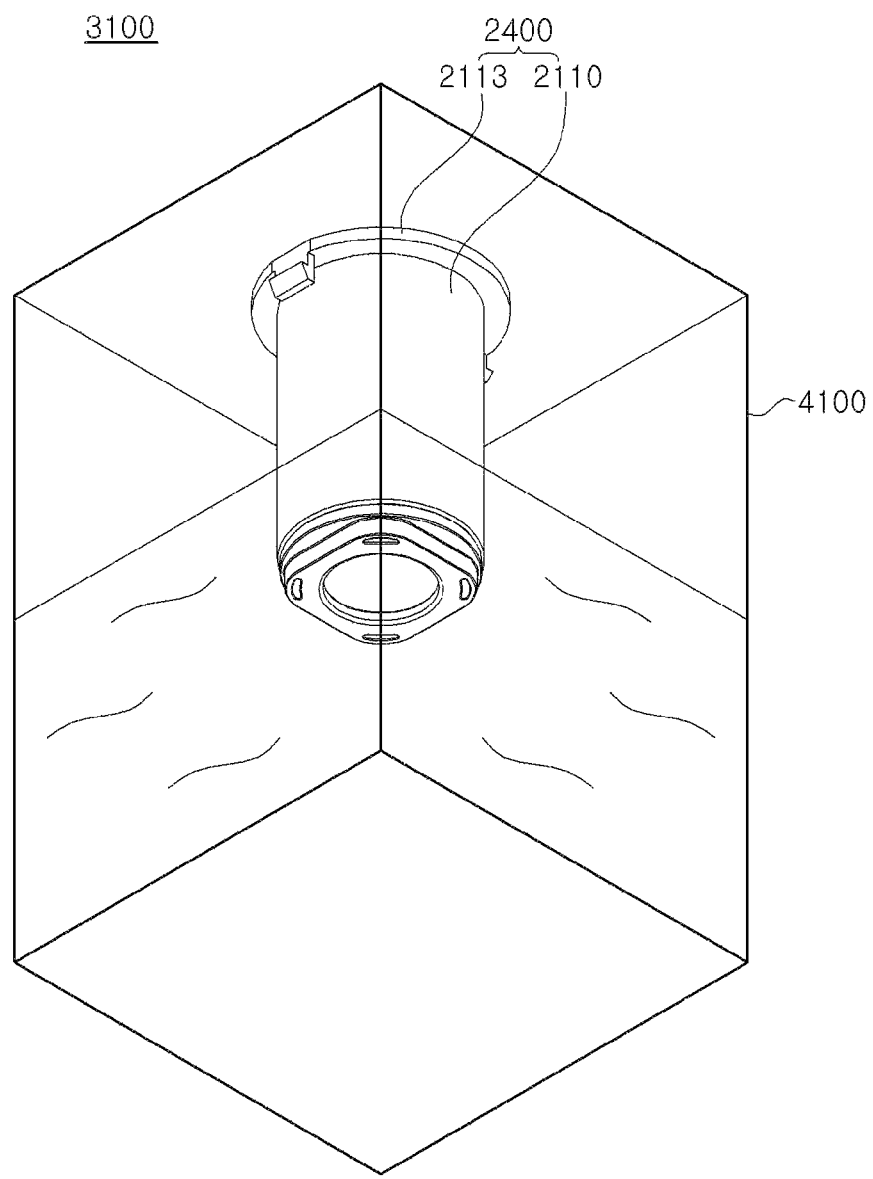
FIG. 30 is a perspective view of a water purifier according to yet another embodiment of the disclosed technology.

FIG. 30 is a perspective view of a water purifier according to yet another embodiment of the disclosed technology.

Referring to FIG. 30, a water purifier 3100 according to this embodiment includes a water reservoir 4100 and a sterilization module 2400 mounted on the water reservoir 4100.

According to this embodiment, a main body 2110 of the sterilization module 2400 has a longer length than the main bodies of the sterilization modules shown in FIG. 15 to FIG. 29. Specifically, the length from a lower surface of the body holding portion 2113 to a lower surface of the main body 2110 is longer than that of each of the sterilization modules shown in FIG. 15 to FIG. 29. That is, the lower surface of the main body 2110 can be immersed in water stored in the water reservoir 4100. For example, the sterilization module 2400 may be formed such that the lower surface of the main body 2110 is placed on the middle line of the water reservoir 4100 or below the middle line thereof. When the lower portion of the sterilization module 2400 is immersed in the water stored in the water reservoir 4100, sterilization of the water occurs.

FIG. 25 and FIG. 30 illustrate the water purifiers in which the sterilization module is mounted on the upper surface of the water reservoir. However, it should be understood that the sterilization module may be mounted on any one of the upper, side and lower surfaces of the water reservoir. Even in the structure wherein the sterilization module is mounted on any surface of the water reservoir, the lower portion of the sterilization module is disposed inside the water reservoir and the upper portion of the sterilization module is disposed outside the water reservoir.

Figure 31:
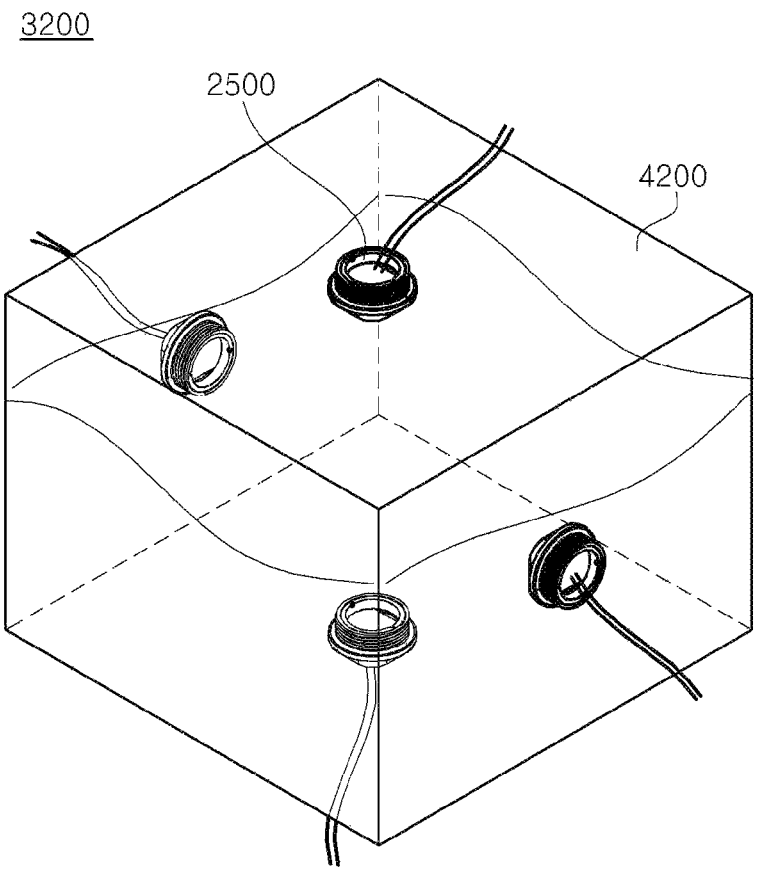
FIG. 31 is a perspective view of a water purifier according to yet another embodiment of the disclosed technology.

FIG. 31 is a perspective view of a water purifier according to yet another embodiment of the disclosed technology.

Referring to FIG. 31, a water purifier 3200 according to this embodiment includes a water reservoir 4200 and a plurality of sterilization modules 2500. The plural sterilization modules 2500 may be selected from among the sterilization modules shown in FIG. 15 to FIG. 29.

According to this embodiment, the sterilization modules 2500 are mounted on an upper surface, a lower surface and both sides of the water reservoir 4200, respectively. In this embodiment, the sterilization module 2500 mounted on the upper surface of the water reservoir 4200 emits UV light towards the surface of water stored in the water reservoir 4200. Further, the sterilization modules 2500 provided to both sides of the water reservoir 4200 emit UV light towards the surface of the water or into the water stored in the water reservoir 4200. Further, the sterilization module 2500 provided to the lower surface of the water reservoir 4200 emits UV light into the water stored in the water reservoir 4200.

Although the water purifier 3200 according to this embodiment is illustrated as including one sterilization module 2500 on each surface of the water reservoir 4200, it should be understood that the water purifier 3200 is not limited thereto. The locations and number of the sterilization modules 2500 in the water purifier 3200 can be changed according to selection of those skilled in the art.

Figure 32:
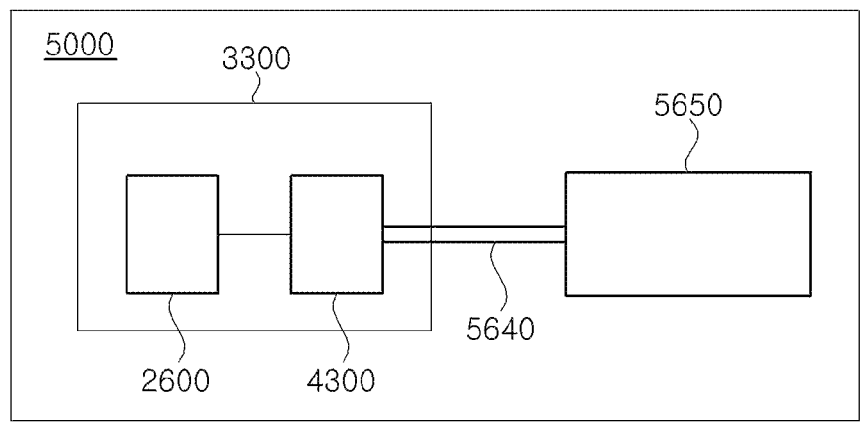
FIG. 32 is a block diagram of a system including a water purifier according to embodiments of the disclosed technology.

FIG. 32 is a block diagram of a system including a water purifier according to embodiments of the disclosed technology.

Referring to FIG. 32, a system 5000 including a water purifier includes a water purifier 3300, a water pipe 5640 and a freezing device 5650. The water purifier 3300 is the water purifier shown in FIG. 25, FIG. 30 or FIG. 31. Thus, repeated description of the water purifier 3300 will be omitted and, for a detailed description of the water purifier 3300, reference can be made to FIG. 25, FIG. 30 or FIG. 31.

According to this embodiment, the system 5000 may be a cooling system such as an ice maker.

According to this embodiment, the system 5000 including a water purifier is configured to purify water using the water purifier 3300 when the water is supplied to the system. Here, the water purifier 3300 purifies the water supplied to the water reservoir 4300 through sterilization using the sterilization module 2600. The purified water is delivered from the water purifier 3300 to the freezing device 5650 through the water pipe 5640. Then, the purified water is cooled into ice by the freezing device 5650 and the ice is stored inside the system 5000 or discharged therefrom.

According to this embodiment, the water pipe 5640 is a channel through which water flows. The water pipe 5640 is connected to the water reservoir 4300 of the water purifier 3300. In addition, the water pipe 5640 is connected to the freezing device 5650.

In FIG. 32, the water reservoir 4300 is illustrated as being connected to the freezing device 5650 through the water pipe. However, it should be understood that the disclosed technology is not limited thereto and other devices may be present between the water reservoir 4300 and the freezing device 5650. In addition, water flow between other devices in the cooling system 5000 may be performed through the water pipe.

Figure 33:
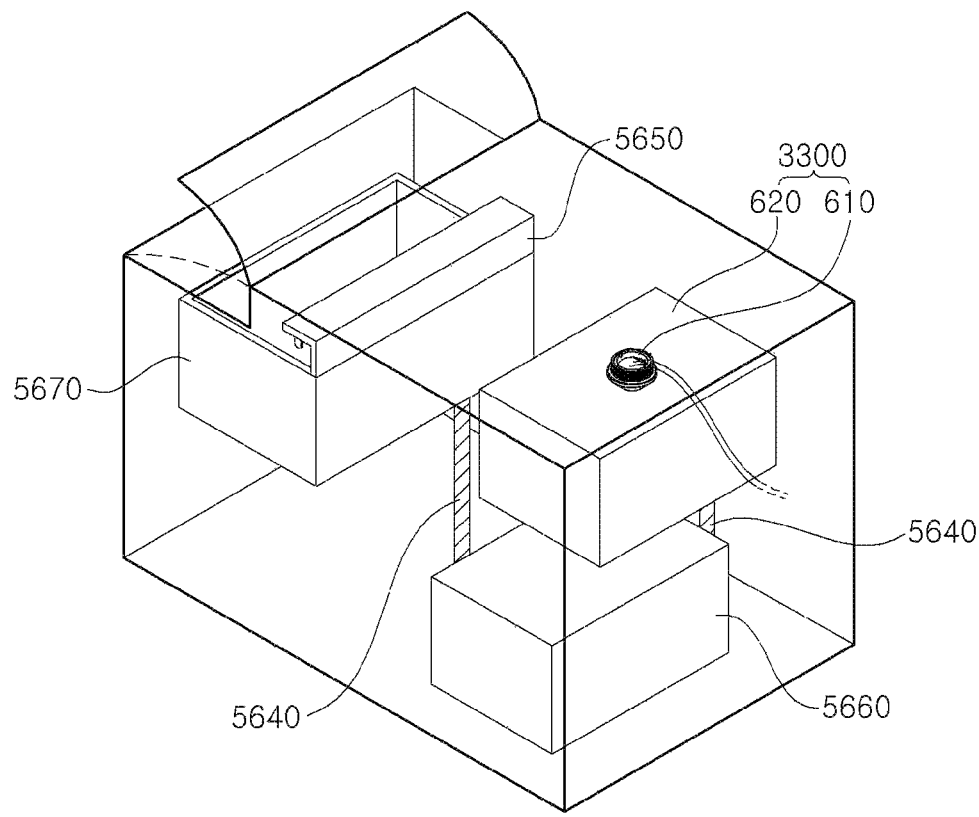
FIG. 33 is a perspective view of the system including the water purifier according to embodiments of the disclosed technology.

FIG. 33 is a perspective view of the system including the water purifier according to embodiments of the disclosed technology.

In FIG. 33, an ice maker is illustrated as the system 5000 including the water purifier. Referring to FIG. 33, the system 5000 includes a water purifier 3300, a cooling device 5660, a freezing device 5650, and a storage unit 5670.

According to this embodiment, the water purifier 3300 purifies water by sterilizing water stored in the water reservoir 4300 using the sterilization module 2600. In FIG. 33, the water purifier 3300 is the water purifier shown in FIG. 25, FIG. 30 or FIG. 31. Thus, repeated description of the water purifier 3300 will be omitted and, for a detailed description of the water purifier 3300, reference can be made to FIG. 25, FIG. 30 or FIG. 31.

The purified water is delivered from the water purifier 3300 to the cooling device 5660. The cooling device 5660 cools the purified water into cold water. The cold water is supplied from the cooling device 5660 to the freezing device 5650. The cold water becomes ice in the freezing device 5650. The ice generated in the freezing device 5650 is stored in the storage unit 5670. Here, water flow between the water purifier 3300, the cooling device 5660 and the freezing device 5650 is achieved through the water pipe 5640.

The freezing device 5650 according to this embodiment is operated by the principle of a typical freezing device. In addition, the freezing device 5650 may employ various ice making and ice melting methods known in the art.

In the system 5000 according to this embodiment, the water purifier 3300 and the cooling device 5660 are separately provided. However, it should be understood that the disclosed technology is not limited thereto. For example, in the system 5000, the cooling device 5660 may be omitted or the water purifier 3300 may be configured to provide the function of the cooling device 5660. In this case, water purified by the water purifier 3300 can be directly supplied to the freezing device 5650.

Figure 34:
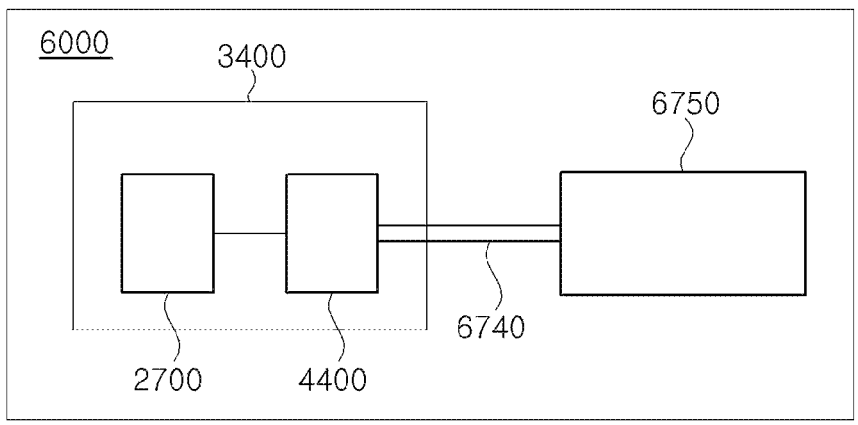
FIG. 34 is a block diagram of a system including a water purifier according to other embodiments of the disclosed technology.

FIG. 34 is a block diagram of a system including a water purifier according to other embodiments of the disclosed technology According to this embodiment, a system including 6000 including a water purifier may be a humidification system such as a humidifier.

According to this embodiment, the system 6000 including a water purifier is configured to purify water using the water purifier 3300 when the water is supplied to the system. Here, the water purifier 3400 purifies the water supplied to the water reservoir 4400 through sterilization using the sterilization module 2700. The purified water is delivered from the water purifier 3400 to a humidifier 6750 through a water pipe 6740. The purified water is changed into water vapor in the humidifier 6750 and the water vapor is discharged from the humidifier 6750.

According to this embodiment, the water pipe 6740 is a channel through which water flows. The water pipe 6740 connects the water reservoir 4400 of the water purifier 3400 to the humidifier 6750.

In FIG. 34, the water reservoir 4400 is illustrated as being connected to the humidifier 6750 through the water pipe. However, it should be understood that the disclosed technology is not limited thereto and other devices may be present between the water reservoir 4400 and the humidifier 6750. In addition, water flow between other devices in the humidification system 6000 may be performed through the water pipe.

Herein, the cooling system and the humidification system are illustrated as the system including a water purifier. However, it should be understood that the system according to the disclosed technology is not limited thereto. The system according to the disclosed technology may be applied to any system using water.

In addition, the sterilization modules, the water purifiers and the systems according to the embodiments of the disclosed technology are illustrated as being configured to purify water. However, it should be understood that the disclosed technology may be applied not only to water sterilization but also to air sterilization.

Although some embodiments have been described herein with reference to the accompanying drawings, it should be understood that these embodiments are provided for illustration only and are not to be construed in any way as limiting the disclosed technology. Therefore, the scope of the present disclosure should be interpreted according to the following appended claims and equivalents thereto.

We claim:

1. A sterilization apparatus comprising:
a main body having an opening at upper and lower sides of the main body;
a protective cover disposed inside the main body to shield an interior of the main body from an outside of the main body, the protective cover including a material through which UV light passes;
an inner holder disposed on the protective cover and fastened to an inner wall of the main body;
a substrate secured to the inner wall of the main body by the inner holder; and
a UV light emitting device disposed on the substrate and configured to emit UV light towards the protective cover,
wherein the inner holder comprises a spacer disposed between the substrate and the protective cover to separate the UV light emitting device from the protective cover and a fixing holder disposed on the substrate and secured to the inner wall of the main body,
wherein the sterilization apparatus further comprises:
a connector disposed on a surface of the substrate and electrically connected to the substrate; and
a cable detachably coupled to the connector,
wherein one end of the cable is detachably coupled to the connector and the other end of the cable is connected to an external power device, and
wherein the connector is at a location deviated from a center of the substrate and the spacer is shaped to expose the connector through an opening formed on a side of the spacer.

2. The sterilization apparatus according to claim 1, wherein the main body has a connection path to connect an upper space over the substrate to a lower space under the substrate.

3. The sterilization apparatus according to claim 2, wherein, when the connector is disposed on a lower surface of the substrate, the one end of the cable is attached to the connector through the connection path.

4. The sterilization apparatus according to claim 1, wherein the fixing holder comprises a depth adjusting portion protruding outward from the fixing holder and restricting a depth at which the fixing holder is coupled to the main body.

5. The sterilization apparatus according to claim 1, wherein the inner holder has an integral structure in which the spacer is integrally connected to the fixing holder.

6. The sterilization apparatus according to claim 5, wherein the spacer includes a groove to receive the substrate, the substrate inserted in the groove.

7. The sterilization apparatus according to claim 5, wherein the inner holder comprises:

a substrate seat protruding inward from an inner wall of the spacer to allow the substrate to be seated thereon; and a substrate holding portion disposed on the substrate and fastened to an inner wall of the fixing holder.

8. The sterilization apparatus according to claim 1, wherein the spacer is separated from the fixing holder, the substrate being inserted between an upper surface of the spacer and a lower surface of the fixing holder, and the fixing holder securing the substrate between the spacer and the fixing holder by compressing the substrate when the fixing holder is fastened to the main body.

9. The sterilization apparatus according to claim 8, wherein the spacer includes a displacement preventing portion protruding upward from an upper surface of the spacer and preventing a dislocation of the substrate, the displacement preventing portion having a height less than or equal to a thickness of the substrate.

10. The sterilization apparatus according to claim 1, further comprising:

a cover seat formed at a lower portion of the main body and protruding inward from an inner surface of the main body such that the protective cover is seated on the cover seat, an inner surface of the cover seat having a tapered shape having a diameter gradually increasing towards a lower surface thereof.

11. The sterilization apparatus according to claim 10, further comprising:

an inner sealing member disposed between an upper surface of the cover seat and a lower surface of the protective cover to seal a gap between the main body and the protective cover.

12. The sterilization apparatus according to claim 1, further comprising:

a body holding portion formed along an outer periphery of the main body to protrude from an outer surface of the main body.

13. The sterilization apparatus according to claim 12, further comprising:

an outer holder fastened to an outer wall of the main body.

14. The sterilization apparatus according to claim 13, further comprising:

an outer sealing member disposed between an upper surface of the body holding portion and a lower surface of the outer holder to seal a gap between the main body and the outer holder.

15. A water purifier comprising:

a water reservoir configured to store water; and a sterilization module disposed to pass through a surface of the water reservoir, and wherein the sterilization module comprises:

a main body having openings at upper and lower sides of the main body the openings penetrating the main body along a first direction extending from the upper side to the lower side of the main body and the main body having a protruding portion inwardly protruding at the lower side of the main body;

a protective cover disposed on the protruding portion of the main body to prevent water from entering into an interior of the main body from an outside of the main body, the protective cover including a material through which UV light passes and extending along a second direction perpendicular to the first direction;

an inner holder disposed on the protective cover and fastened to an inner wall of the main body;

a substrate secured to the inner wall of the main body by the inner holder; and a UV light emitting device disposed on the substrate and emitting UV light towards the protective cover, and wherein the inner holder comprises a spacer disposed between the substrate and the protective cover to separate the UV light emitting device from the protective cover and a fixing holder disposed on the substrate and secured to the inner wall of the main body.

16. The water purifier according to claim 15, wherein the sterilization module further comprises: a body holding portion formed along an outer periphery of the main body and protruding from an outer surface of the main body; and an outer holder fastened to an outer wall of the main body, an upper surface of the body holding portion contacting an inner surface of the water reservoir, a lower surface of the outer holder contacting an outer surface of the water reservoir.

* * * * *